(12) United States Patent
Volpe et al.

(10) Patent No.: US 10,960,213 B2
(45) Date of Patent: Mar. 30, 2021

(54) VERIFICATION OF CARDIAC ARRHYTHMIA PRIOR TO THERAPEUTIC STIMULATION

(71) Applicant: ZOLL MEDICAL CORPORATION, Chelmsford, MA (US)

(72) Inventors: Shane S. Volpe, Saltsburg, PA (US); Regis George, Aliquippa, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 172 days.

(21) Appl. No.: 15/917,982

(22) Filed: Mar. 12, 2018

(65) Prior Publication Data
US 2019/0275335 A1  Sep. 12, 2019

(51) Int. Cl.
*A61N 1/365* (2006.01)
*A61N 1/362* (2006.01)
(Continued)

(52) U.S. Cl.
CPC ....... *A61N 1/36507* (2013.01); *A61N 1/0484* (2013.01); *A61N 1/3625* (2013.01);
(Continued)

(58) Field of Classification Search
CPC .............. A61N 1/36507; A61N 1/3904; A61N 1/0484; A61N 1/3625; A61N 1/3987;
(Continued)

(56) References Cited

U.S. PATENT DOCUMENTS

| 3,460,542 A | 8/1969 | Gemmer |
| 3,744,482 A | 7/1973 | Kaufman et al. |

(Continued)

FOREIGN PATENT DOCUMENTS

| EP | 0395242 | 10/1990 |
| EP | 396048 | 11/1990 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

(Continued)

*Primary Examiner* — Erin M Piateski
(74) *Attorney, Agent, or Firm* — Finch & Maloney PLLC

(57) ABSTRACT

Ambulatory medical devices may occasionally improperly administer a therapeutic stimulation pulse to a patient upon an incorrect detection of arrhythmia in the patient. To address these improperly administered therapeutic stimulation pulses, an ambulatory medical device includes processes and systems for verifying an initial declaration of an arrhythmia. The ambulatory medical device described include at least one first sensing electrode and at least one second sensing electrode distinct from the at least one first sensing electrode. First electrocardiogram (ECG) signals detected by the first sensing electrode are analyzed to provide an initial declaration of the arrhythmia condition of the patient. As a treatment protocol is being initiated in response to the analysis of the first ECG signals, second ECG signals detected by the second sensing electrode are analyzed to verify the initial declaration of the arrhythmia.

13 Claims, 17 Drawing Sheets

(51) Int. Cl.
  *A61N 1/04* (2006.01)
  *A61N 1/39* (2006.01)
  *A61B 5/024* (2006.01)
  *A61B 5/00* (2006.01)
  *A61B 5/0452* (2006.01)
  *A61B 5/0408* (2006.01)

(52) U.S. Cl.
  CPC ......... *A61N 1/3904* (2017.08); *A61N 1/3968* (2013.01); *A61N 1/3987* (2013.01); *A61B 5/02427* (2013.01); *A61B 5/0452* (2013.01); *A61B 5/04087* (2013.01); *A61B 5/746* (2013.01)

(58) Field of Classification Search
  CPC ............ A61B 5/02427; A61B 5/04087; A61B 5/0452; A61B 5/746
  USPC .......................................................... 607/7
  See application file for complete search history.

(56) References Cited

U.S. PATENT DOCUMENTS

| | | |
|---|---|---|
| 3,826,245 A | 7/1974 | Funfstuck |
| 4,002,239 A | 1/1977 | Buchalter |
| 4,094,310 A | 6/1978 | McEachern et al. |
| 4,136,690 A | 1/1979 | Anderson et al. |
| 4,422,459 A | 12/1983 | Simson |
| 4,458,691 A | 7/1984 | Netravali |
| 4,576,170 A | 3/1986 | Bradley et al. |
| 4,580,572 A | 4/1986 | Granek et al. |
| 4,583,547 A | 4/1986 | Granek et al. |
| 4,729,377 A | 3/1988 | Granek et al. |
| 4,928,690 A | 5/1990 | Heilman et al. |
| 4,949,719 A | 8/1990 | Pless et al. |
| 4,991,217 A | 2/1991 | Garrett et al. |
| 5,000,189 A | 3/1991 | Throne et al. |
| 5,062,834 A | 11/1991 | Gross et al. |
| 5,078,134 A | 1/1992 | Heilman et al. |
| 5,350,401 A | 9/1994 | Levine |
| 5,558,098 A | 9/1996 | Fain |
| 5,718,242 A | 2/1998 | McClure et al. |
| 5,741,306 A | 4/1998 | Glegyak et al. |
| 5,772,604 A | 6/1998 | Langberg et al. |
| 5,827,196 A | 10/1998 | Yeo et al. |
| 5,929,601 A | 7/1999 | Kaib et al. |
| 5,944,669 A | 8/1999 | Kaib |
| 6,065,154 A | 5/2000 | Hulings et al. |
| 6,097,982 A | 8/2000 | Glegyak et al. |
| 6,148,233 A | 11/2000 | Owen et al. |
| 6,178,343 B1 | 1/2001 | Bindszus et al. |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,374,138 B1 | 4/2002 | Owen et al. |
| 6,406,426 B1 | 6/2002 | Reuss et al. |
| 6,546,285 B1 | 4/2003 | Owen et al. |
| 6,681,003 B2 | 1/2004 | Linder et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 6,961,612 B2 | 11/2005 | Elghazzawi et al. |
| 7,149,579 B1 | 12/2006 | Koh et al. |
| 7,295,871 B2 | 11/2007 | Halperin et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,534,212 B2 | 5/2009 | Baker, Jr. |
| 7,712,373 B2 | 5/2010 | Nagle et al. |
| 7,715,916 B2 | 5/2010 | Haefner |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,005,552 B2 | 8/2011 | Covey et al. |
| 8,121,683 B2 | 2/2012 | Bucher et al. |
| 8,140,154 B2 | 3/2012 | Donnelly et al. |
| 8,160,698 B2 | 4/2012 | Elghazzawi et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,161,723 B2 | 10/2015 | Rodriguez-Llorente et al. |
| 9,283,399 B2 | 3/2016 | Donnelly et al. |
| 10,646,707 B2 * | 5/2020 | Volosin ................ A61B 5/0006 |
| 2001/0031991 A1 | 10/2001 | Russial |
| 2003/0004547 A1 | 1/2003 | Owen et al. |
| 2003/0032988 A1 | 2/2003 | Fincke |
| 2003/0095648 A1 | 5/2003 | Kaib et al. |
| 2005/0049644 A1 | 3/2005 | Warren et al. |
| 2005/0131465 A1 | 6/2005 | Freeman et al. |
| 2005/0288599 A1 | 12/2005 | MacAdam et al. |
| 2006/0178706 A1 | 8/2006 | Lisogurski et al. |
| 2006/0211934 A1 | 9/2006 | Hassonjee et al. |
| 2007/0016029 A1 | 1/2007 | Donaldson et al. |
| 2007/0073120 A1 | 3/2007 | Li et al. |
| 2007/0239220 A1 | 10/2007 | Greenhut et al. |
| 2008/0004536 A1 | 1/2008 | Baxi et al. |
| 2008/0033495 A1 | 2/2008 | Kumar |
| 2008/0183090 A1 | 7/2008 | Farringdon et al. |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0076363 A1 | 3/2009 | Bly et al. |
| 2009/0076559 A1 | 3/2009 | Libbus et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0114243 A1 | 5/2010 | Nowak et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0170692 A1 | 7/2011 | Konrad et al. |
| 2011/0202101 A1 | 8/2011 | Tan et al. |
| 2011/0288604 A1 | 11/2011 | Kaib et al. |
| 2011/0288605 A1 * | 11/2011 | Kaib ................ A61B 5/1118 607/5 |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0025131 A1 | 1/2014 | Sullivan et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0303680 A1 | 10/2014 | Donnelly et al. |
| 2014/0324112 A1 | 10/2014 | Macho et al. |

(56) References Cited

U.S. PATENT DOCUMENTS

| | | | |
|---|---|---|---|
| 2015/0035654 A1 | 2/2015 | Kaib et al. | |
| 2015/0039042 A1 | 2/2015 | Amsler et al. | |
| 2015/0039053 A1 | 2/2015 | Kaib et al. | |
| 2015/0080699 A1 | 3/2015 | Kaib et al. | |
| 2015/0224330 A1 | 8/2015 | Kaib et al. | |
| 2015/0265164 A1 | 9/2015 | Gopalakrishnan et al. | |
| 2016/0270738 A1* | 9/2016 | Volpe | A61B 5/7278 |
| 2018/0078779 A1* | 3/2018 | An | A61N 1/39622 |
| 2018/0093102 A1 | 4/2018 | Sullivan et al. | |
| 2018/0146870 A1* | 5/2018 | Shemesh | A61B 5/02416 |

FOREIGN PATENT DOCUMENTS

| | | |
|---|---|---|
| EP | 1720446 | 11/2006 |
| JP | 5115450 | 5/1993 |
| JP | 2002-514107 | 5/2002 |
| JP | 2008-302228 | 12/2008 |
| JP | 2008302225 | 12/2008 |
| JP | 2009510631 | 3/2009 |
| WO | 8304171 | 12/1983 |
| WO | 1998039061 | 9/1998 |
| WO | 2004054656 | 7/2004 |
| WO | 2004078259 | 9/2004 |
| WO | 2006050325 | 5/2006 |
| WO | 2009122277 | 10/2009 |
| WO | 2010077997 | 7/2010 |
| WO | 2012006524 | 1/2012 |
| WO | 2013040214 | 3/2013 |
| WO | 2013130957 | 9/2013 |
| WO | 2014097035 | 6/2014 |
| WO | 2016098062 | 6/2016 |

OTHER PUBLICATIONS http://web.archive.org/web/20030427001846/http:/www.lifecor.comiimagelib/imageproduct.asp.publiehsed by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particluar Requirements for the Safety of Cardiac Defibrillators (including Automated External Defibrillators) 2004, ISBN 1-57020-210-9; abstract; p. vi; p. 50, section 107.1.2.

Zoll Medical Corporation, LifeVest Model WCD 3000 Operator's Manual, Pittsburgh, PA.

L.A. Geddes et al., "Principles of Applied Biomedical Instrumentation", 3rd Edition, 1968, Chapter 9, pp. 315-377.

Enrique Spinelli et al., "A Capacitive Electrode with Fast Recovery Feature", Institute of Physics and Engineering in Medicine, 2012 pp. 1277-1288.

David M. Beams, "Pacemaker Sense Amplifiers", University of Wisconsin, 2014, Chapter 8, 48 pages.

Zoll Medical Corporation, "LifeVest TruVector Arrhythmia Detection Algorithm", 2017, rev 20c0010_revh; 8 pages.

* cited by examiner

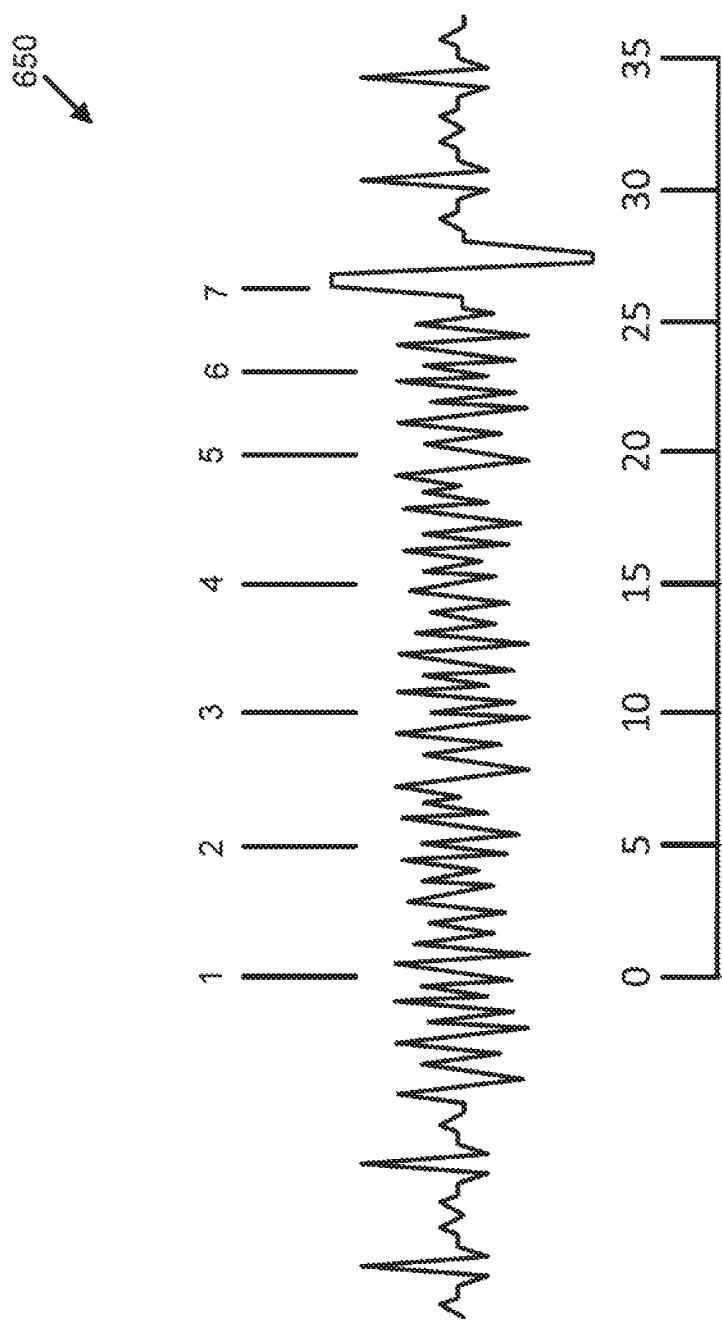

VERIFICATION OF CARDIAC ARRHYTHMIA PRIOR TO THERAPEUTIC STIMULATION

BACKGROUND

The present disclosure is related to detection of abnormal cardiac events and treatment of cardiac arrhythmias.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the deadliest cardiac arrhythmias include ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation (VF), ventricular tachycardia (VT), pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying therapeutic stimulation pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL® LifeVest® wearable cardioverter defibrillator available from ZOLL® Medical Corporation, and the AED Plus also available from ZOLL® Medical Corporation.

SUMMARY

In at least one example, an ambulatory medical device is provided. The ambulatory medical device includes a pair of therapy electrodes; first and second pairs of sensing electrodes, and at least one processor coupled to the pair of therapy electrodes and the first and second pairs of sensing electrodes. The pair of therapy electrodes is configured to couple externally to a skin of a patient and to provide one or more therapeutic stimulation pulses to a heart of the patient during execution of a treatment protocol. The first pair of sensing electrodes is configured to couple externally to the skin of the patient and to acquire first electrocardiogram (ECG) signals. The second pair of sensing electrodes is distinct from the first pair of sensing electrodes and is configured to couple externally to the skin of the patient to acquire second ECG signals having an improved reliability over the first ECG signals. The at least one processor is configured to receive first ECG data generated from the first ECG signals; analyze the first ECG data to detect an arrhythmia condition of the patient; record an initial declaration of the arrhythmia condition of the patient in response to detecting the arrhythmia condition; initiate the treatment protocol in response to the initial declaration of the arrhythmia condition; receive second ECG data generated from the second ECG signals; and analyze the second ECG data to verify the initial declaration of the arrhythmia condition.

In the ambulatory medical device, the at least one processor may be further configured to abort the treatment protocol in response to detecting normal cardiac function based on analysis of the second ECG data. The at least one processor may be further configured to control delivery of the one or more therapeutic stimulation pulses to the heart of the patient in response to verifying the initial declaration of the arrhythmia condition.

In the ambulatory medical device, the first pair of sensing electrodes may include dry sensing electrodes. The second pair of sensing electrodes may include an electrically conductive sensing element configured to be electrically coupled to the skin of the patient via a conductive gel.

The ambulatory medical device may further include a gel dispenser. The gel dispenser may be configured to dispose gel between an electrically conductive element of the second pair of sensing electrodes and the skin of the patient. The ambulatory medical device may further include gel deployment circuitry coupled to the at least one processor, and the at least one processor may be further configured to signal the gel deployment circuitry to cause at least one gel dispenser to apply conductive gel between the skin of the patient and the second pair of sensing electrodes in response to detecting the arrhythmia condition and prior to acquiring the second ECG signals.

The ambulatory medical device may further include a pair of electrode assemblies including the second pair of sensing electrodes and the at least one gel dispenser. The ambulatory medical device may further include a pair of therapy pads including the at least one gel dispenser and the pair of therapy electrodes. The pair of therapy electrodes may include the second pair of sensing electrodes.

In the ambulatory medical device, the at least one processor may be configured to analyze the first ECG data with an abnormality detection process and to analyze the second ECG data with an arrhythmia verification process. The ambulatory medical device may further include at least one non-ECG sensor, the at least one non-ECG sensor including one or more of an accelerometer and a photoplethysmograph sensor. The at least one processor may be further coupled to the at least one non-ECG sensor and be further configured to receive non-ECG data generated from signals acquired by the at least one non-ECG sensor; and analyze the non-ECG data with the abnormality detection process to contribute to detection of the arrhythmia condition.

In another example, another ambulatory medical device is provided. This ambulatory medical device includes a pair of sensing electrodes, a pair of multi-function electrodes, and at least one processor coupled to the pair of sensing electrodes and the pair of multi-function electrodes. The pair of sensing electrodes is configured to couple externally to a skin of a patient and to acquire first electrocardiogram (ECG) signals to detect an arrhythmia condition of the patient. The pair of multi-function electrodes is configured to couple externally to the skin of the patient and to provide one or more therapeutic stimulation pulses to a heart of the patient during execution of a treatment protocol and to acquire second ECG signals to verify the arrhythmia condition of the patient. The at least one processor is coupled to the pair of sensing electrodes and the pair of multi-function electrodes and is configured to receive first ECG data generated from the first ECG signals; analyze the first ECG data to detect the arrhythmia condition of the patient using an abnormality detection process; record an initial declaration of the arrhythmia condition of the patient in response to detecting the arrhythmia condition; initiate the treatment protocol in response to the initial declaration; receive second ECG data generated from the second ECG signals; and analyze the second ECG data to either verify or refute the initial declaration of the arrhythmia condition using an arrhythmia verification process distinct from the abnormality detection process.

In the ambulatory medical device, the at least one processor may be further configured to delay the treatment protocol in response to refuting the initial declaration of the arrhythmia condition. The at least one processor may be further configured to abort the treatment protocol in response to determining that normal rhythm has returned in the patient. The at least one processor may be further configured to control delivery of the one or more therapeutic stimulation pulses to the heart of the patient in response to verifying the initial declaration of the arrhythmia condition.

The ambulatory medical device may further include gel deployment circuitry coupled to the at least one processor. The at least one processor may be further configured to signal the gel deployment circuitry to cause at least one gel dispenser to apply conductive gel between the skin of the patient and the pair of multi-function electrodes in response to detecting the arrhythmia condition and prior to acquiring the second ECG signals.

The ambulatory medical device may further include a pair of electrode assemblies including the pair of multi-function electrodes and the at least one gel dispenser. The ambulatory medical device may further include a pair of therapy pads including the at least one gel dispenser and a pair of therapy electrodes, wherein the pair of multi-function electrodes comprise the pair of therapy electrodes.

The ambulatory medical device may further include at least one non-ECG sensor. The at least one non-ECG sensor may include one or more of an accelerometer and a photoplethysmograph sensor. The at least one processor may be further coupled to the at least one non-ECG sensor and be further configured to receive non-ECG data generated from signals acquired by the at least one non-ECG sensor and analyze the non-ECG data using the abnormality detection process to contribute to detection of the arrhythmia condition.

In another example, another ambulatory medical device is provided. The ambulatory medical device includes a pair of therapy electrodes, first and pairs of sensing electrodes, gel deployment circuitry, and at least one processor coupled to the first and second pairs of sensing electrodes, the pair of therapy electrodes, and the gel deployment circuitry. The pair of therapy electrodes is configured to couple externally to a skin of a patient and to provide one or more therapeutic stimulation pulses to a heart of the patient during execution of a treatment protocol. The first pair of sensing electrodes is configured to couple externally to the skin of the patient and to acquire first electrocardiogram (ECG) signals. The second pair of sensing electrodes is distinct from the first pair of sensing electrodes and is configured to couple externally to the skin of the patient and to acquire second ECG signals. The at least one processor is coupled to the first pair of sensing electrodes, the second pair of sensing electrodes, the pair of therapy electrodes, and the gel deployment circuitry and is configured to receive first ECG data generated from the first ECG signals, analyze the first ECG data to detect an arrhythmia condition of the patient, record an initial declaration of the arrhythmia condition of the patient in response to detecting the arrhythmia condition, initiate the treatment protocol in response to the initial declaration of the arrhythmia condition, signal the gel deployment circuitry to cause at least one gel dispenser to apply conductive gel between the second pair of sensing electrodes and the skin of the patient prior to acquiring the second ECG signals, receive second ECG data generated from the second ECG signals, analyze the second ECG data to verify the initial declaration of the arrhythmia condition, either abort or delay the treatment protocol in response to at least one of detecting normal cardiac function and refuting the initial declaration of the arrhythmia condition based on analysis of the second ECG data, and control delivery of the one or more therapeutic stimulation pulses to the heart of the patient in response to verifying the initial declaration of the arrhythmia condition.

In the ambulatory medical device, the first pair of sensing electrodes may include dry sensing electrodes. The second pair of sensing electrodes may include conductive sensing electrodes.

In another example, another ambulatory medical device is provided. The ambulatory medical device includes a pair of therapy electrodes, a pair of sensing electrodes, ECG sensing electrode circuitry coupled to the pair of sensing electrodes, and at least one processor coupled to the pair of sensing electrodes, the ECG sensing electrode circuitry, and the pair of therapy electrodes. The pair of therapy electrodes is configured to couple externally to a skin of a patient and to provide at least one therapeutic stimulation pulse to a heart of the patient. The pair of sensing electrodes is configured to couple externally to the skin of the patient and to acquire first and second of electrocardiogram (ECG) signals from the patient. The ECG sensing electrode circuitry is configured to process the acquired first and second ECG signals from the patient to generate first and second ECG data. The at least one processor is and configured to receive the first ECG data; analyze the first ECG data using a first process to detect an arrhythmia condition of the patient; record an initial declaration of the arrhythmia condition of the patient in response to detecting the arrhythmia condition; initiate a treatment protocol in response to the initial declaration of the arrhythmia condition, the treatment protocol specifying provision of at least one alarm indicating an imminent delivery of at least one therapeutic stimulation pulse and provision of the at least one therapeutic stimulation pulse; cause the ECG sensing electrode circuitry to activate a second process distinct from the first process to analyze the second ECG signals; receive the second ECG data; and analyze, after the provision of the at least one alarm and before the provision of the at least one therapeutic stimulation pulse, the second ECG data using the second process distinct from the first process to verify the initial declaration of the arrhythmia condition.

In the ambulatory medical device, the second process may be configured to have improved reliability in analyzing the second ECG signals to verify the initial declaration of the arrhythmia condition. The at least one processor may be further configured to control delivery of the at least one therapeutic stimulation pulse in response to verifying the initial declaration of the arrhythmia condition. The at least one processor may be further configured to refute, using the second ECG data, the initial declaration of the arrhythmia condition and delay the provision of the at least one therapeutic stimulation pulse in response to refuting the initial declaration of the arrhythmia condition. The delay may include a delay having a duration between 30 seconds and 45 seconds. The at least one processor may be configured to analyze the second ECG data using the second process at least in part by determining a value that indicates a confidence that the second ECG data reflects normal cardiac function of the patient and evaluate the value. The at least one processor may be configured to evaluate the value at least in part by comparing the value to a threshold value.

In ambulatory medical device, the first process may include an abnormality detection process, and the second process may include an arrhythmia verification process. The abnormality detection process may include a first number of sub-processes, and the arrhythmia verification process may include a second number of sub-processes less than the first number of sub-processes. The abnormality detection process may include a first set of sub-processes, and the arrhythmia verification process may include a second set of sub-processes different than the first set of sub-processes. The arrhythmia verification process may include at least one of a heart rate detection sub-process and a signal morphology detection sub-process. The abnormality detection process may include a first fast Fourier transform, and the arrhythmia verification process may omit a second fast Fourier transform.

In the ambulatory medical device, the at least one processor is configured to cause the ECG sensing electrode circuitry to activate the second process to analyze the second ECG signals within of a predefined period of time after the initial declaration of the arrhythmia condition. The predefined period of time may have a duration inclusively between 1 and 60 seconds. The predefined period of time may varies based on the arrhythmia condition. Where the arrhythmia condition is ventricular tachycardia, the predefined period of time may include 8 to 10 seconds. Where the arrhythmia condition is ventricular fibrillation, the predefined period of time may include 5 to 8 seconds.

The ambulatory medical device may further include at least one non-ECG sensor. The at least one non-ECG sensor may include one or more of an accelerometer and a photoplethysmograph sensor. The at least one processor may be further coupled to the at least one non-ECG sensor and may be further configured to receive non-ECG data generated from signals acquired by the at least one non-ECG sensor and analyze the non-ECG data with the abnormality detection process to contribute to detection of the arrhythmia condition. The ambulatory medical device may further include a garment housing the pair of sensing electrodes and the second process may include a process to tighten the garment around the patient.

BRIEF DESCRIPTION OF THE DRAWINGS

Various aspects of one or more examples are discussed below with reference to the accompanying drawings, which are not intended to be drawn to scale. The drawings are included to provide an illustration and a further understanding of these various aspects and examples. The drawings are incorporated in and constitute a part of this specification but are not intended to limit the scope of the disclosure. The drawings, together with the remainder of the specification, serve to explain principles and operations of the described and claimed aspects and examples. For purposes of clarity, not every component may be labeled in every figure.

FIG. 6B depicts a monitoring and treatment protocol including an alarm sequence in accordance with at least one example disclosed herein.

DETAILED DESCRIPTION

Overview

Figure 1:
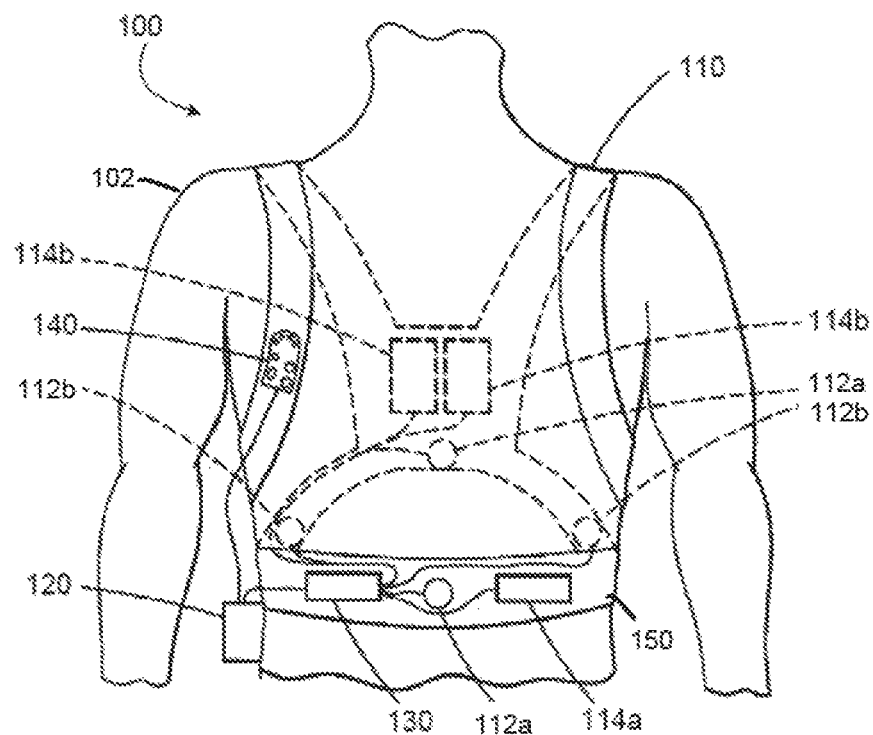
FIG. 1 depicts a wearable, ambulatory, external medical device in accordance with at least one example disclosed herein.

The present disclosure is directed to verification of a cardiac arrhythmia condition, such as tachycardia or fibrillation, prior to administering one or more electrical therapeutic stimulation pulses to a patient using an ambulatory medical device.

Some ambulatory medical devices can identify a cardiac abnormality (e.g., a cardiac arrhythmia) and deliver one or more therapeutic electrical pulses to correct the detected abnormality. These devices represent a significant diagnostic and therapeutic advance. With these ambulatory medical devices, the cardiac function of a patient may be continuously monitored and therapeutic stimulation pulses administered even while providing some freedom of movement to the patient.

Despite these significant advantages, conventional ambulatory medical devices may occasionally improperly administer a therapeutic stimulation pulse as a result of detecting an abnormality that is not an arrhythmia condition. To prevent these improperly administered therapeutic stimulation pulses, examples described herein include ambulatory medical devices having processes, mechanisms, and systems for verifying an initial declaration of an arrhythmia condition prior to administering a therapeutic stimulation pulse.

For instance, to verify an initial arrhythmia declaration, some example ambulatory medical devices described herein include a plurality of sensing electrode pairs. This plurality of sensing electrode pairs may include a first electrode pair and a second electrode pair distinct from the first electrode pair. The first electrode pair may detect first electrocardiogram (ECG) signals, and the second electrode pair may detect second ECG signals. In some examples, the ambulatory medical devices are configured to execute one or more abnormality detection and arrhythmia verification processes using these distinct electrode pairs and ECG signals. These one or more abnormality detection and arrhythmia verification processes may initially determine whether an arrhythmia condition is present and later verify the arrhythmia condition remains present prior to administering a therapeutic stimulation pulse.

More specifically, in some examples, the ambulatory medical device is configured to execute an abnormality detection process using the first electrode pair. During the abnormality detection process, the ambulatory medical device acquires and processes first ECG signals detected by the first electrode pair. Processing the acquired first ECG signals generates associated first ECG data, which may be analyzed to detect an abnormality (e.g., an arrhythmia condition). Where the analyzed first ECG data indicates an arrhythmia condition, the ambulatory medical device initially declares the presentation of an arrhythmia condition (e.g., stores one or more bits of a specific value at a specific memory location) and initiates a treatment process. This treatment process may include a variety of actions.

For instance, in one example of the treatment process, the ambulatory medical device first issues an alarm to indicate that the ambulatory medical device has detected an abnormality and declared an arrhythmia condition. The alarm may include auditory, tactile, and/or visual components. The alarm may further indicate that the patient must respond to the alarm within a predetermined time frame (e.g., 60 seconds) if the patient wishes to avoid treatment. If the patient responds as indicated (e.g., by pushing a specific response button provided by the ambulatory medical device within the predetermine time frame), the ambulatory medical device delays or aborts treatment. However, in some examples, if the patient fails to respond within the predetermined time frame, the ambulatory medical device continues execution of the treatment protocol.

In some examples, the next step of the treatment protocol is deployment of conductive gel between the skin of the patient and one or more pairs of electrodes (e.g., sensing and/or treatment electrode pairs). This step is executed to decrease the impedance between the electrode pairs and the patient's skin. In some examples, the conductive gel is deployed between one or more pairs of treatment electrodes and the patient's skin. In some examples, the conductive gel is deployed between one or more pairs of sensing electrodes (e.g., the second electrode pair) and the patient's skin. In some examples, the conductive gel is deployed between one or more pairs of treatment electrodes and the patient's skin and between one or more pairs of sensing electrodes and the patient's skin. In some examples, the conductive gel is deployed between one or more pairs of multi-function electrodes (e.g., electrodes configured to function as both treatment and sensing electrodes) and the patient's skin. Other types of electrodes may be involved within the gel deployment process, and the examples disclosed herein are not limited to particular types of electrode pairs. After completion of (or during) gel deployment, the treatment protocol may continue with additional alarms that instruct bystanders not to touch the patient.

In some examples of the treatment protocol, the ambulatory medical device next charges its capacitors and, optionally, issues another alarm to clearly warn of an imminent delivery of a therapeutic stimulation pulse. According to some examples, the treatment protocol culminates with the delivery of the therapeutic stimulation pulse to the patient's skin via a pair of treatment electrodes and the conductive gel. After the treatment protocol is complete, the ambulatory medical device returns to execution of the abnormality detection process.

In some examples, the ambulatory medical device implements (e.g., during execution of the treatment protocol) an arrhythmia verification process using the second electrode pair. During execution of the arrhythmia verification process, the ambulatory medical device acquires and processes second ECG signals detected by the second electrode pair. Processing the acquired second ECG signals generates associated second ECG data, which may be analyzed to verify the arrhythmia condition. Where the ambulatory medical device is able to verify the initial arrhythmia declaration using the analyzed second ECG data, the ambulatory medical device continues the treatment protocol. However, where the ambulatory medical device is unable to verify the initial arrhythmia declaration using the analyzed second ECG data, the ambulatory medical device suspends the treatment protocol and returns to execution of the abnormality detection process.

In examples, the second ECG signals have a higher reliability and are therefore more likely to accurately indicate the actual occurrence of an arrhythmia condition. In an example, the higher reliability of the second ECG signals relative to the first ECG signals can be accomplished by, for example, using a different type of sensor for the second electrode pair compared to the first electrode pair. While the first electrode pair can use a dry ECG electrode sensing mechanism, the second electrode pair can use a different mechanism (e.g., a wet, gel based conductive sensing mechanism). In some examples, a sensing mechanism for the second electrode pair is selected to be more accurate than the sensing mechanism for the first electrode pair. Regardless of the sensing mechanism, accuracy of the first electrode pair and the second electrode pair may be optionally improved by administering a conductive gel between skin of the patient and the second electrode pair to improve quality of the sensed ECG signals. In examples, the higher reliability of the second ECG signals relative to the first ECG signals can be accomplished by, for example, applying different analyses to the second ECG data, such as those that increase a statistical confidence level of a conclusion drawn from the analyzed second ECG data. These analyses may use stricter criteria for identifying an arrhythmia condition, may process longer samples of the second ECG data than the samples of first ECG data previously processed, may process more samples of the second ECG data than the samples of the first ECG data previously processed, and/or may process an overall amount of second ECG data that is greater than the amount of first ECG data previously processed. Details of such additional analyses are provided below. In examples, the physical conditions under which the second ECG signals are obtained (e.g., that improve electrical contact between the patient and the second electrode pair) are improved so as to improve reliability compared to the first ECG signals.

An advantage of examples described herein includes improved patient comfort and health by reducing unnecessary treatment based on false positive detections of arrhythmia conditions. Another advantage of examples described herein includes improved ambulatory medical device performance by reducing the number of times an unnecessary therapeutic stimulation pulse is administered to a patient, which then reduces the frequency with which electrical storage systems in the ambulatory medical device are recharged and other components are refurbished (e.g., replenishment of conductive gel reservoirs, replacement of therapy electrodes, etc.).

Example Medical Devices

The teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device is capable of continuous use by the patient. For example, the wearable medical device can be configured to be worn by a patient for as many as 24 hours a day. In some implementations, the continuous use may be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. One illustration of a sporadic period in which use of the wearable medical device temporarily and briefly ceases is when the patient removes the wearable medical device for a short portion of the day (e.g., for half an hour) to bathe.

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provide specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), heart sounds, breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be configured to couple externally to a skin of a patient, such as by attaching the electrode to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient (also referred to herein as a "multi-function" electrode). In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the external surface of the skin of the patient on the front of the patient's torso to deliver pacing or defibrillating therapy. Similarly, the back adhesively attachable therapy electrode attaches to the external surface of the skin of the patient on the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

Figure 2:
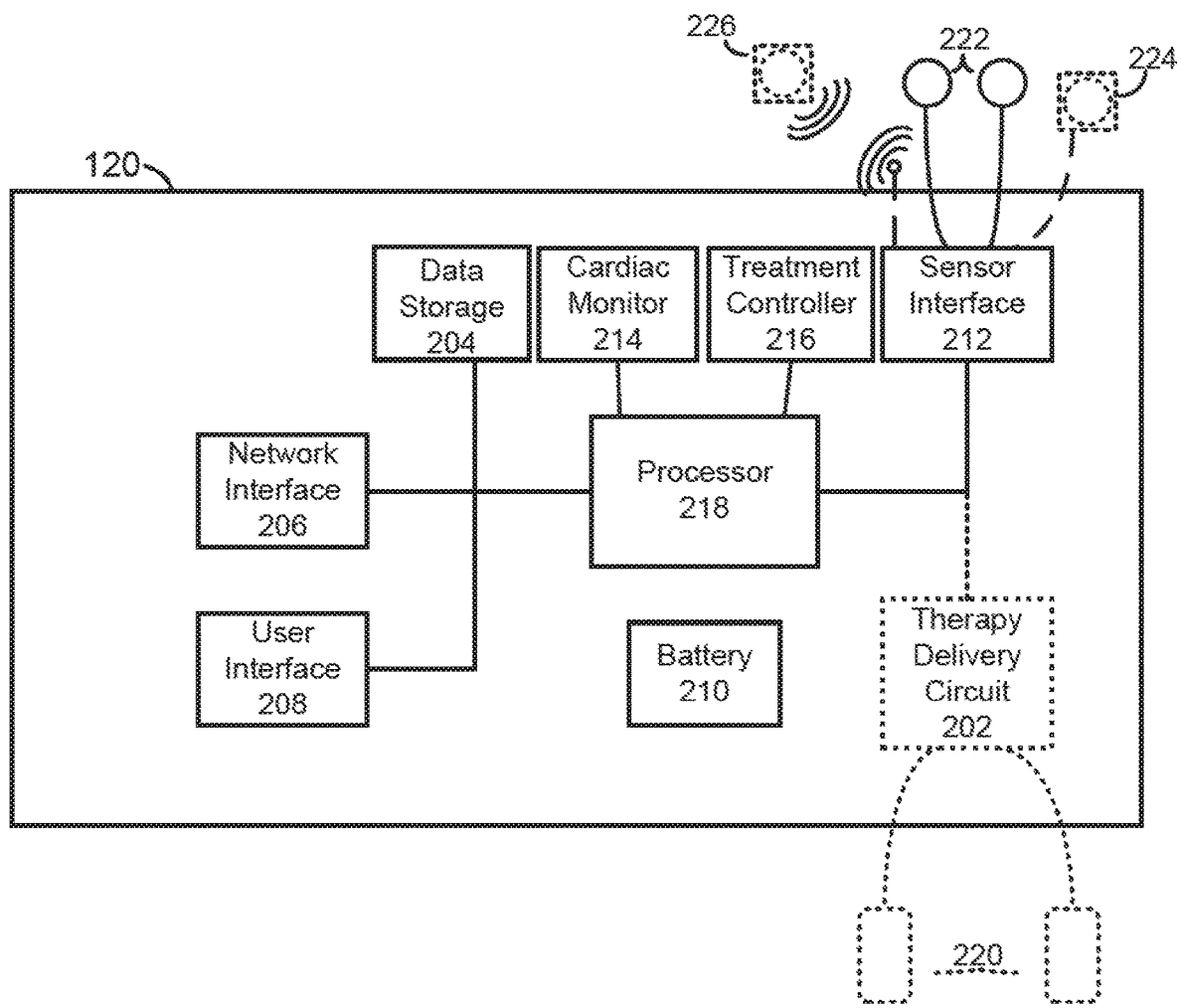
FIG. 2 depicts an arrangement of components of a medical device controller in accordance with at least one example disclosed herein.

In some implementations, the medical device may be a patient monitoring device with separable treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. The treatment or therapy functions may be contained in a separate module that may be coupled or decoupled as appropriate for individual patients. For example, cardiac physiological parameters monitored by such a device may include a patient's electrocardiogram (ECG) information, heart sounds (e.g., using accelerometers or microphones), and other related cardiac information. The patient may carry such a cardiac monitoring device with separable treatment or therapy functions as the patient goes about a daily routine. For example, in the usual course of wear such a device may include the cardiac monitor portion (without treatment or therapy functions) and may be configured to detect the patient's ECG through a plurality of cardiac sensing electrodes. The cardiac monitor may be attached to a patient via a plurality of (e.g., two or more) adhesive cardiac sensing electrodes disposed about the patient's torso. Such cardiac monitors are used in remote mobile cardiac monitoring applications, such as continuous cardiac event monitoring. For example, such monitors may be used in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a response button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others. If a treatment and/or therapeutic function is deemed necessary, such as when the cardiac monitor indicates that the patient is at an increased risk of a treatable arrhythmia, the patient may be directed to attach a treatment module containing the therapy delivery circuit 202 and associated therapy electrodes 220 (FIG. 2). Examples of such treatable arrhythmias can include paceable conditions such as bradycardia, tachycardia, and other irregular rhythm conditions, or conditions that require a defibrillation shock such as VT or VF.

FIG. 1 illustrates an example medical device 100 that is external, ambulatory, and wearable by a patient 102, and configured to implement one or more configurations described herein. For example, the medical device 100 can be a non-invasive medical device configured to detect an arrhythmia condition using at least one first sensing electrode, verify whether the initial detected arrhythmia is correct or refute the initial declaration, and either provide a therapeutic stimulation pulse to the heart of the patient or return to a monitoring mode, respectively depending on the result of the verification. Such a medical device 100 can be, for example, an ambulatory medical device that is capable of, and designed for, moving with the patient as the patient goes about his or her daily routine. For example, the medical device 100, such as the LifeVest® wearable cardioverter defibrillator available from ZOLL® Medical Corporation, as described herein can be bodily-attached to the patient. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic stimulation pulses to the patient. For example, such therapeutic stimulation pulses (also referred to as electrical signals or shocks) can be pacing, defibrillation, or transcutaneous electrical nerve stimulation (TENS) pulses.

The medical device 100 can include one or more of the following: a garment 110, one or more sensing electrode pairs 112 (e.g., anterior/posterior electrodes 112a and side/side electrodes 112b), one or more therapy electrodes pairs 114 (e.g., anterior therapy electrode 114a and posterior electrodes 114b), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which in turn can be affixed to the garment 110 (e.g., assembled into the garment 110 or removably attached to the garment using, for example, hook and loop fasteners). In some implementations, the sensing electrodes 112 can be permanently integrated into the garment 110. The medical device controller 120 can be operatively coupled to a pair of therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

The sensing electrodes 112 can be configured to detect one or more cardiac signals. Examples of such signals include ECG signals, heart sounds, and/or other sensed cardiac physiological signals from the patient. The sensing electrodes 112 can also be configured to detect other types of patient physiological parameters, such as tissue fluid levels, lung sounds, respiration movement and/or sounds, patient movement, etc. Example sensing electrodes 112 include dry electrodes with an oxide coating such as tantalum pentoxide electrodes, as described in, for example, U.S. Pat. No. 6,253,099 titled "Cardiac Monitoring Electrode Apparatus and Method," which is hereby incorporate herein by reference in its entirety.

Example sensing electrodes 112 also include conductive electrodes with a foundational layer (e.g., made of foam), an electrically conductive element (e.g., made of tin, silver-silver chloride, etc.), and an electrolytic layer (e.g., made of hydrogel) that electrically couples the conductive element to the patient's skin. In some examples, the therapy electrodes 114 can also be configured to include sensors configured to detect ECG signals as well as other physiological signals of the patient. In an example, one or more of the sensing electrodes 112 and the therapy electrodes 114 are comprised within an electrode assembly. In an example, an electrode assembly includes a plurality of electrodes and a corresponding plurality of electrical conductors formed on a dielectric film. Each respective electrode includes a conductive element that defines a contact area of the respective electrode. The conductive elements may be formed by depositing a conductive material on the dielectric film. The electrical conductors may be formed integrally with the conductive elements on the dielectric film or they may be formed separately and electrically connected to the conductive elements. The electrical conductors may be covered with an insulating layer to electrically isolate them from an upper surface of the adhesive film layer and the subject's skin. Moreover, details regarding the construction of an ECG electrode that may be included in the electrode assembly can be found in U.S. Patent Application Publication No. 2013/0325096 titled "Long Term Wear Multifunction Biomedical Electrode," which is hereby incorporated herein by reference in its entirety.

In some examples, the electrode assembly and/or the electrodes it comprises are included within a sensor assembly. Such a sensor assembly may include other, non-ECG sensors described herein, such as the heart sounds sensors 224 and/or the tissue fluid sensors 226 described below with reference to FIG. 2. In certain examples, the sensor assembly also includes non-ECG sensors such as a pulse oximeter that measures arterial oxygen saturation via a plethysmograph sensor, such as a photoplethysmograph (PPG) sensor.

In examples, a therapy electrode 114 can be constructed to include at least one conductive gel dispenser that, upon instruction by gel dispenser circuitry and a processor, applies conductive gel so that it is disposed between a skin of the patient and a therapy electrode. While the term "therapy electrode" is used herein, it will be understood that this term may be equivalently substituted with "therapy pad" when application of conductive gel is also described.

The connection pod 130 can, in some examples, include a signal processor configured to amplify, filter, and digitize cardiac signals sensed by the sensing electrodes 112 prior to transmitting the cardiac signals to the medical device controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device 100.

Example Medical Device Controller

FIG. 2 illustrates a sample component-level view of the medical device controller 120 as initially shown in FIG. 1. As shown in FIG. 2, the medical device controller 120 can include a therapy delivery circuit 202, a data storage 204, a network interface 206, a user interface 208, at least one battery 210, a sensor interface 212, cardiac monitor 214, a treatment controller 216, and least one processor 218.

The therapy delivery circuit 202 can be coupled to one or more electrodes 220 configured to provide therapy to the patient (e.g., therapy electrodes 114a-b as described above in connection with FIG. 1). For example, the therapy delivery circuit 202 can include, or be operably connected to, circuitry components that are configured to generate and provide the therapeutic electrical pulse or shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic stimulation pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between a 350 to 500 volt surge rating and can be charged in approximately 15 to 30 seconds from a battery pack, such as the at least one battery 210.

For example, each defibrillation pulse can deliver between 60 to 180 joules of energy. In some implementations, the defibrillating pulse can be a biphasic truncated exponential waveform, whereby the pulse can switch between a positive and a negative portion (e.g., charge directions). This type of waveform can be effective at defibrillating patients at lower energy levels when compared to other types of therapeutic stimulation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device.

In certain implementations, the user interface 208 can include one or more physical interface devices such as input devices, output devices, and combination input/output devices and a software stack configured to drive operation of the devices. These user interface elements may render visual, audio, and/or tactile content, including content relating to location-specific processing. Thus, the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), heart sounds sensors 224, and tissue fluid monitors 226 (e.g., based on ultra-wide band radiofrequency devices). As such, the sensor interface 212 may include amplifiers and analog to digital converters to condition and digitize signals acquired by the sensors.

The ECG electrodes 222 can monitor a patient's ECG information. For example, the ECG electrodes 222 can be galvanic, conductive and/or dry electrodes configured to measure changes in a patient's electrophysiology to measure the patient's ECG information. The ECG electrodes 222 can transmit information descriptive of the ECG signals to the sensor interface 212 for subsequent analysis.

The heart sounds sensors 224 can detect a patient's heart sound information. For example, the heart sounds sensors 224 can be configured to detect heart sound values including any one or all of S1, S2, S3, and S4. From these heart sound values, certain heart sound metrics may be calculated, including any one or more of electromechanical activation time (EMAT), percentage of EMAT (% EMAT), systolic dysfunction index (SDI), and left ventricular systolic time (LVST). The heart sounds sensors 224 can include an acoustic sensor configured to detect sounds from a subject's cardiac system and provide an output signal responsive to the detected heart sounds. The heart sounds sensors 224 can also include a multi-channel accelerometer, for example, a three-channel accelerometer configured to sense movement in each of three orthogonal axes such that patient movement/body position can be detected and correlated to detected heart sounds information. The heart sounds sensors 224 can transmit information descriptive of the heart sounds information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by heart sounds sensor 224 and transmitted to the sensor interface 212, the sensor interface 212 can transmit the data to the processor 218 which, in turn, relays the data to the cardiac monitor 214 and/or the treatment controller 216. These data can also be stored on the data storage 204.

According to some examples illustrated by FIG. 2, the cardiac monitor 214 is configured to initiate and control monitoring of a patient's cardiac function and coordinate identification of arrhythmias experienced by the patient. When instructing mechanisms that perform these functions, in some examples the cardiac monitor 214 detects arrhythmias by analyzing ECG data received from the sensor interface 212 for patterns (e.g. heart rates) indicative of arrhythmias. Responsive to identifying a data pattern indicative of an arrhythmia, the cardiac monitor 214 initiates action by the treatment controller 216. In some examples, the cardiac monitor 214 analyzes additional, non-ECG data received from the sensor interface 212 to ascertain the patient's physical condition. For instance, the cardiac monitor 214 may analyze PPG data to determine oxygen saturation of the patient's blood. The cardiac monitor 214 may also analyze accelerometer data to determine patient movement and/or heart sounds. Patient movement may, in turn, indicate a general lack of body movement and/or respiration.

According to some examples illustrated by FIG. 2, the treatment controller 216 is configured to initiate and control treatment of an arrhythmia identified by the cardiac monitor 214. When executing according to this configuration, in some examples, the treatment controller 216 executes a treatment protocol specific to the particular identified arrhythmia. For instance, the treatment controller 216 may pace a patient experiencing bradycardia or ventricular tachycardia or may defibrillate a patient experiencing atrial or ventricular fibrillation. In some examples, the treatment controller 216 initiates deployment of electrically conductive gel as part of the treatment protocol. Also, in some examples, the treatment controller 216 monitors the reaction of the patient's heart to the treatment protocol and takes further action based on the reaction of the patient's heart. This further action may include altering the treatment protocol and/or escalating notifications to external parties.

Both the cardiac monitor 214 and the treatment controller 216 can be implemented using hardware or a combination of hardware and software. For instance, in some examples, the cardiac monitor 214 and/or the treatment controller 216 are implemented as software components that are stored within the data storage 204 and executed by the processor 218. In this example, the instructions included in the cardiac monitor 214 and/or the treatment controller 216 can cause the processor 218 to monitor for, detect, and treat arrhythmias. In other examples, the cardiac monitor 214 and/or the treatment controller 216 are application-specific integrated circuits (ASICs) that are coupled to the processor 218 and configured to monitor for, detect, and treat arrhythmias. Thus, in examples the cardiac monitor 214 and the treatment controller 216 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring, treatment, etc.), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

Example Arrhythmia Verification Systems, Devices, and Processes

As described above, some examples disclosed herein include an ambulatory medical device (e.g., the medical device 100) configured to monitor a patient for cardiac abnormalities, detect and declare arrhythmia conditions, and verify arrhythmia declarations prior to treating the patient with one or more therapeutic pulses. This verification improves patient comfort, for example by avoiding needless therapeutic intervention. In some examples, the at least one processor executes an abnormality detection process when analyzing first ECG data based on first ECG signals and executes an arrhythmia verification process to analyze second ECG data based on second ECG signals.

To detect an abnormality, declare an arrhythmia condition, and verify an arrhythmia declaration, some example ambulatory medical devices described herein statically and/or dynamically associate electrodes into a plurality of electrode pairs. This plurality of electrode pairs may include a first electrode pair and a second electrode pair distinct from the first electrode pair. The first electrode pair detects first ECG signals, and the second electrode pair detects second ECG signals. In some examples, the ambulatory medical devices are configured to execute one or more abnormality detection and arrhythmia verification processes using these distinct electrode pairs and ECG signals. These processes may initially determine whether an arrhythmia condition is present and later verify the arrhythmia condition remains present prior to administering a therapeutic stimulation pulse.

More specifically, in some examples, the ambulatory medical device is configured to execute a cardiac abnormality detection process using the first electrode pair. During the abnormality detection process, the ambulatory medical device acquires and processes first ECG signals detected by the first electrode pair. Processing the acquired first ECG signals generates associated first ECG data, which may be analyzed to detect an abnormality (e.g., an arrhythmia condition). Where the analyzed first ECG data indicates an arrhythmia condition, the ambulatory medical device records an initial declaration of the arrhythmia condition and initiates a treatment protocol. As described above, this treatment protocol may include acts such as issuing an alarm to indicate that the ambulatory medical device has detected an arrhythmia condition, deploying conductive gel where no response to the alarm is received, charging capacitors, issuing a final warning to bystanders, and delivering a therapeutic stimulation pulse. After the treatment protocol is complete, the ambulatory medical device returns to execution of the abnormality detection process.

In some examples, the ambulatory medical device implements (e.g., during execution of the treatment protocol) an arrhythmia verification process using the second electrode pair. The arrhythmia verification process may be executed, for example, just prior to delivering the therapeutic stimulation pulse (e.g., after application of the conductive gel between the second electrode pair and the patient's skin). The presence of the conductive gel increases the quality of the electrical connection between the electrodes and the patient's skin. Thus, the presence of the gel may aid the function of a therapy electrode in providing therapeutic stimulation pulses to the patient's heart. Similarly, the presence of the gel may aid a sensing electrode in acquiring ECG signals descriptive of the patient's cardiac activity. During execution of the arrhythmia verification process, the ambulatory medical device acquires and processes second ECG signals detected by the second electrode pair. Processing the acquired second ECG signals generates associated second ECG data, which may be analyzed to verify the arrhythmia condition. Where the ambulatory medical device is able to verify the initial arrhythmia declaration using the analyzed second ECG data, the ambulatory medical device continues the treatment protocol. However, where the ambulatory medical device is unable to verify the initial arrhythmia declaration using the analyzed second ECG data, the ambulatory medical device suspends the treatment protocol and returns to execution of the abnormality detection process.

Although some examples focus on the use of ECG data for the abnormality detection and arrhythmia verification, other examples use other data in addition to, or as a replacement of, the ECG data. This other data may include PPG and/or accelerometer data. How these examples utilize this data is described further below.

To implement the abnormality detection and arrhythmia verification processes, some examples of the ambulatory medical device include a medical device controller (e.g., the medical device controller 120) and one or more pairs of electrodes. In these examples, the medical device controller may include least one processor (e.g., processor 218) that is in electrical communication with the first and second electrode pairs to acquire the first and second ECG signals. The at least one processor is configured to process the first ECG signals to generate first ECG data and to analyze the first ECG data to detect abnormalities and declare arrhythmia conditions. The at least one processor is also configured to process the second ECG signals to generate second ECG data and to analyze the second ECG data to verify initial declarations of arrhythmia conditions. The first ECG signals and the second ECG signals may be acquired during distinct and/or overlapping time intervals.

The first and second electrode pairs may include therapy electrodes (e.g., therapy electrodes 114), sensing electrodes (e.g., sensing electrodes 112), multi-function electrodes (i.e., electrodes that include elements that enable application as both a sensing electrode and a therapy electrode) or some hybrid combination of differing types. The electrodes may include conductive ECG electrodes and/or dry ECG electrodes.

A dry electrode can include a metal substrate with an oxide coating deposited on the substrate. For example, such a dry electrode can include tantalum-tantalum pentoxide electrodes, as described in, for example, U.S. Pat. No. 6,253,099 titled "Cardiac Monitoring Electrode Apparatus and Method," which is hereby incorporated herein by reference in its entirety. For example, a dry electrode can be constructed by forming a tantalum metal substrate and depositing a tantalum pentoxide layer on the metal surface. An anodizing process can be used to form the oxide layer. The oxide layer can cover an entire surface of the metal substrate including the outer edges. Such a dry electrode can be placed directly on a patient's skin to acquire ECG signals without the presence of an electrolyte. A dry electrode can be regarded as having characteristics close to a polarizable electrode, for example, because no actual charge transfers across the electrode interface. In this sense, a dry electrode behaves like a capacitor where it can be regarded as sensing displacement current across the electrode interface rather than actual charge transfer across the interface.

Figure 3:
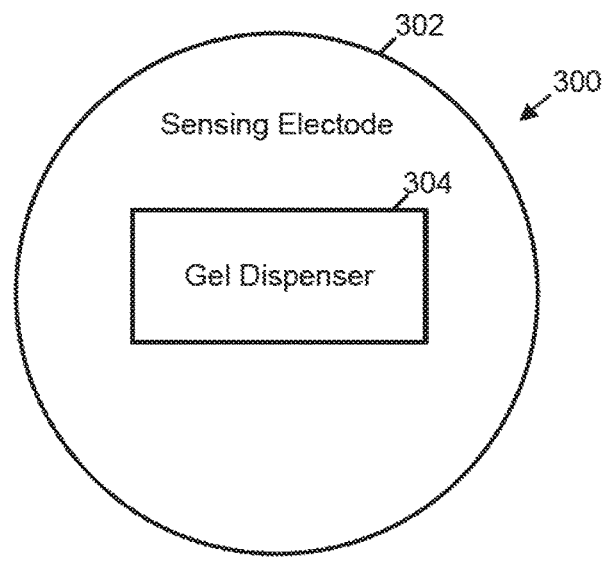
FIG. 3 depicts a sensing electrode in accordance with at least one example disclosed herein.

Conductive sensing electrodes, on the other hand, include an electrically conductive element (e.g., made of tin, silver-silver chloride, etc.), and an electrolytic gel (e.g., hydrogel) that electrically couples the conductive element to the patient's skin. For example, the hydrogel may be combined with an adhesive material to facilitate close coupling to the patient's skin. In other implementations, the gel may be stored in a gel dispenser that is configured to deploy when needed as described in detail below (FIG. 3). A conductive electrode can be regarded as having characteristics close to a nonpolarizable electrode, for example, because the conductive electrode senses actual charge transfer or current that passes across the electrode-electrolytic interface based on ionic conduction on the patient's skin.

Figure 4:
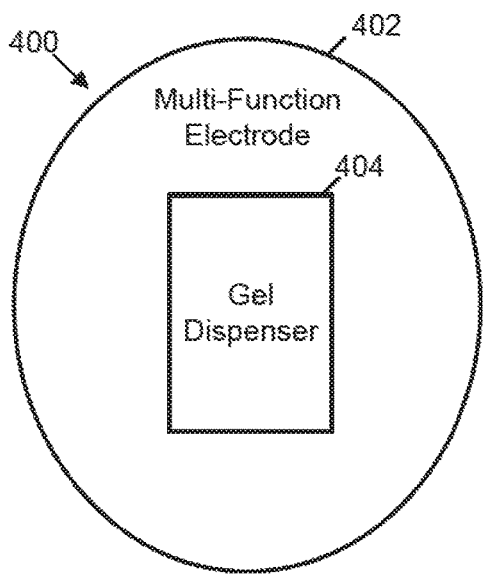
FIG. 4 depicts a multi-function electrode in accordance with at least one example disclosed herein.
Figure 5:
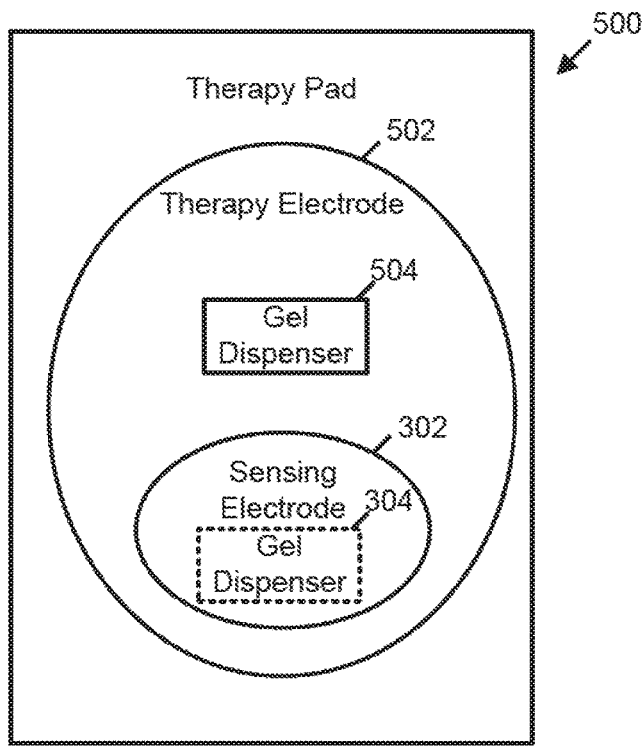
FIG. 5 depicts a therapy pad in accordance with at least one example disclosed herein.

In some examples, the ambulatory medical device is configured to execute the abnormality detection process using ECG data based on signals acquired by dry sensing electrodes and to execute the arrhythmia verification process using ECG data based on signals acquired by conductive sensing electrodes. Dry sensing electrodes are described above with reference to FIGS. 1 and 2. FIG. 3 illustrates a conductive sensing electrode that may be incorporated into some examples. FIG. 4 illustrates a conductive multi-function electrode that may be incorporated into some examples. FIG. 5 illustrates a therapy pad and electrode that may be incorporated into some examples and that may be used as a conductive sensing electrode.

FIG. 3 illustrates an electrode assembly 300 that comprises a conductive sensing electrode 302. The conductive sensing electrode 302 may include a foundational layer (e.g., made of foam), an electrically conductive element (e.g., made of tin, silver-silver chloride, etc.) held in electrical contact with the patient's skin, and a gel dispenser 304 configured to dispense electrically conductive gel between the electrically conductive element and the patient's skin. The conductive sensing electrode 302 may acquire ECG signals that are conditioned and processed by the ambulatory medical device to determine the patient's cardiac condition. This conditioning and processing generates ECG data based on the ECG signals. The ECG signals have an improved reliability over ECG signals acquired by dry sensing electrodes because of use of gel.

The gel dispenser 304 is coupled to and under the control of a treatment controller (e.g., the treatment controller 216). An electrolytic gel layer of the sensing electrode 302 is applied by the gel dispenser 304 under control of the treatment controller during execution of the treatment protocol. The gel dispenser 304 may include, for example, a gel reservoir that is ruptured to dispose the gel between the electrically conductive element of the sensing electrode 302 and the skin of the patient.

FIG. 4 illustrates another example of an electrode assembly 400 that includes a multi-function electrode 402 and a gel dispenser 404. The multi-function electrode 402 may include a foundational layer (e.g., made of foam), an electrically conductive element made of a metal (e.g., made of tin, silver-silver chloride, etc.), and an electrolytic layer (e.g., made of hydrogel) that electrically couples the conductive element to the patient's skin. The multi-function electrode 402 may acquire ECG signals that are conditioned and processed by the ambulatory medical device to determine the patient's cardiac condition. This conditioning and processing generates ECG data based on the ECG signals. The ECG signals may have an improved reliability over ECG signals acquired by dry sensing electrodes. The multi-function electrode 402 may also provide one or more therapeutic stimulation pulses to the skin of the patient.

The gel dispenser 404 is coupled to and under the control of the treatment controller. In some examples of the electrode assembly 400, the electrolytic layer of the multi-function electrode 402 is applied by the gel dispenser 404 under control of the treatment controller during execution of the treatment protocol. The gel dispenser 404 may include, for example, a gel reservoir that is ruptured to dispose the gel between the electrically conductive element of the multi-function electrode 402 and the skin of the patient.

FIG. 5 illustrates a therapy pad 500 that incorporates one or more of the elements of the therapy electrodes 114 described above with reference to FIG. 1. As shown in FIG. 5, the therapy pad 500 may include both a therapy electrode 502 and a sensing electrode 302. In some examples, the therapy pad 500 is configured to dispose gel in a manner that prevents the gel from acting as a direct electrical connection between the therapy electrode 502 and the electrode of the sensing electrode 302. In some examples of the therapy pad 500, the gel dispenser 504 operates under control of the treatment controller and, during execution of the treatment protocol, disposes a layer of electrically conductive gel between the therapy electrode 502 (and in some examples, the sensing electrode 302) and the skin of the patient. As shown in FIG. 5, the therapy pad 500 may include the gel dispenser 304. In this example, the gel dispenser 304 is optional as indicated by its rendering in dashed line. As described above, the gel dispenser 304 may dispose a layer of electrically conductive gel between the sensing electrode 302 and the skin of the patient. In some examples, the metal layer of the therapy electrode 502 is used as a conductive sensing electrode as well as a therapy electrode. In other examples, a portion of the therapy electrode 502 is electrically isolated from the remainder of the therapy electrode 502 and incorporates a distinct sensing electrode, such as the sensing electrode 302. As described above, the sensing electrode 302 may acquire ECG signals that are conditioned and processed by the medical device to determine the patient's cardiac condition. The therapy electrode 502 may provide one or more therapeutic stimulation pulses to the patient.

Although FIGS. 3-5 depict conductive sensing, multi-function, and therapy electrodes, examples are not limited to these types of electrodes. For instance, some examples may use the same or different pairs of dry sensing electrodes to acquire both the first and second ECG signals. Other combinations will be apparent in view of the present disclosure. In addition, as described above with reference to FIGS. 1 and 2, the electrode assemblies 300 and 400 and the therapy pad 500 may include other types of sensors used to detect other physiologic parameters. For example, the electrode assemblies and therapy pad may include PPG and/or accelerometric sensors that detect oxygen saturation of the patient's blood, patient respiration, and other patient movement.

Figure 6A:
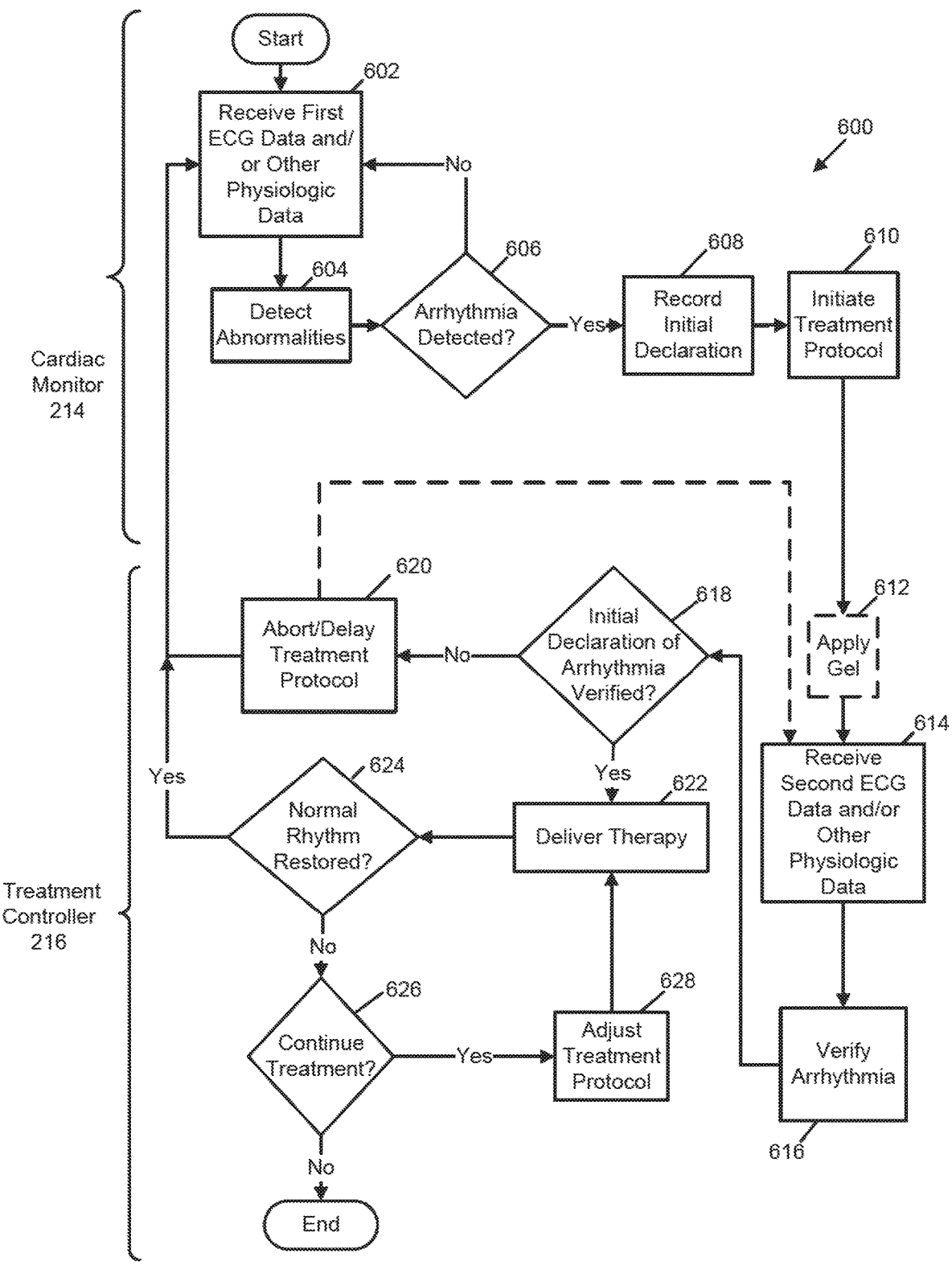
FIG. 6A depicts a monitoring and treatment process including arrhythmia verification in accordance with at least one example disclosed herein.

The various example medical devices described above may execute one or more monitoring and treatment processes that verify a cardiac arrhythmia condition prior to administering a therapeutic stimulation pulse. FIG. 6A illustrates one example of such a monitoring and treatment process 600 executed in some examples. The monitoring and treatment process 600 starts with a cardiac monitor 214 of an ambulatory medical device 100 receiving 602 first ECG data based on first ECG signals acquired by a first pair of electrodes. This first pair of electrodes may include one or more sensing electrodes (e.g., sensing electrodes 112 or ECG electrodes 222), one or more therapy electrodes, and/or one or more multi-function electrodes configured to include sensing capability and therapy capability (i.e., the administration of therapeutic stimulation pulses). In some examples of act 602, the cardiac monitor 214 receives other data indicative of other patient physiologic parameters, such as oxygen saturation, respiration, and/or other movement.

Next, the cardiac monitor attempts to detect abnormalities 604 in the first ECG data and/or the other patient physiologic data by executing an abnormality detection process. This abnormality detection process may include various sub-processes, as described further below with reference to Table 1 and FIGS. 7 and 8. Where the cardiac monitor does not detect 606 an arrhythmia condition, the cardiac monitor returns to receiving 602 first ECG data. However, upon detecting 606 that the patient is experiencing an arrhythmia condition, the cardiac monitor records 608 an initial arrhythmia declaration (e.g., by storing one or more bits at a specific memory location) and initiates 610 a treatment protocol based on the type of arrhythmia condition detected.

In some examples, initiation 610 of the treatment protocol includes issuance of an alarm (e.g., an auditory alarm, a tactile alarm, a visual alarm, or a combination thereof) of an impending therapeutic stimulation pulse. This alarm enables the patient to correct an otherwise erroneous arrhythmia declaration and enables people proximate to the patient to take appropriate action (e.g., avoid physical and electrically conductive contact with the patient, call medical support staff, etc.).

In some examples the treatment protocol includes identifying the arrhythmia condition detected and selecting a therapeutic stimulation pulse best suited to correct the detected arrhythmia condition. Parameters for the therapeutic stimulation pulse to be applied that can vary between different types of arrhythmia condition include the periodicity with which a therapeutic stimulation pulse is delivered, a voltage, a current, a phase, a waveform, and a duration, among other parameters. In some examples, the treatment protocol includes provision, by a treatment controller (e.g., the treatment controller 216), of one or more control signals to associated processors, circuitry, and/or systems of the ambulatory medical device 100 to initiate 610 a treatment protocol for the provision to the patient of the selected therapeutic stimulation pulse.

In one example, after initiation 610 of the treatment protocol, the treatment controller controls, via a gel dispenser and associated circuitry, optional application 612 of conductive gel between the patient's skin and one or more of a first sensing electrode pair, a second sensing electrode pair, a multi-function electrode pair, a therapy electrode pair or any combination thereof. As described above, conductive gel can improve the electrical contact (and therefore conductivity) between an electrode and the skin of the patient, thus improving the therapeutic quality of the applied stimulation pulse while also reducing the risk of injury (such as topical burning or scorching) to the patient. The optional application 612 of conductive gel can also improve the quality (e.g., signal to noise ratio) of a second ECG signal detected by one or more of a first sensing electrode pair, a second sensing electrode pair, and/or a multi-function electrode pair.

The conductive gel may be applied 612 in response to an instruction from the treatment controller to gel deployment circuitry. Upon receiving the instruction (e.g., a control signal) from the treatment controller, the gel deployment circuitry causes at least one gel dispenser to apply conductive gel between at least one of a first sensing electrode pair, a second sensing electrode pair, and a multi-function electrode pair and the skin of the patient prior to acquiring second ECG signals, as described herein.

Regardless of whether gel is applied 612, the monitoring and treatment process 600 continues with the treatment controller receiving 614 second ECG data based on second ECG signals acquired by a second pair of electrodes. This second pair of electrodes may be in contact with the conductive gel and may include one or more sensing electrodes (e.g., sensing electrode pairs 112 or ECG electrodes 222), one or more therapy electrodes, and/or one or more multi-function electrodes configured to include sensing capability and therapy capability (i.e., the administration of therapeutic stimulation pulses). When using distinct electrode pairs to detect and acquire the first ECG signals and the second ECG signals, the first sensing electrode pair and the second sensing electrode pair may rely on different electrodes to detect the ECG signals. In an example, the first pair of sensing electrodes operates using a dry sensing electrode where the second pair of sensing electrodes (or therapy or multi-function electrodes) operates using a conductive sensing electrode. In an example, the arrhythmia condition detection mechanism used by the second electrode pair is selected so that it has a higher reliability than that used by the first electrode pair, as described above.

Next, the treatment controller attempts to verify 616 the declared arrhythmia 616 using the second ECG data by executing an arrhythmia verification process. For example, the second process to verify the arrhythmia can be initiated as soon as one second after the initial declaration of the arrhythmia. In some examples, the second process to verify the arrhythmia can be initiated in time periods of between around 2 to 10 seconds, 10 to 30 seconds, 30 to 45 seconds, 45 seconds to 60 seconds, or 60 seconds to 120 seconds after the initial declaration of the arrhythmia. In some cases, if the patient responds via one or more response buttons, or otherwise is detected by the treatment controller as being conscious, the initiation of the second process to verify the arrhythmia can be delayed by an additional period of time (e.g., an additional 30 to 45 seconds) beyond the time periods specified above. One or more of these time periods can be preconfigured during an initial setup of the device (e.g., by a technician or a patient service representative). For instance, the time periods can be stored in memory or other data storage as one or more user-configurable values. In some examples, these one or more user-configurable values include a first value and a second value. The first value specifies a time period that the treatment controller is configured to wait between the initial declaration of the arrhythmia and initiation of the second process. The second value specifies a time period by which the treatment controller is configured to delay initiation of the second process in response to detecting that the patient is conscious (e.g., by a user action such as when the patient presses the one or more response buttons).

The arrhythmia verification process may include various sub-processes, as described with reference to Table 1 and FIGS. 7 and 9. In an example, the verification 616 of the second ECG data results in a more reliable determination of whether or not the patient is experiencing an arrhythmia condition. Furthermore, as indicated above, the phrases "more reliable," "higher reliability," and "improved reliability" can include using different processing algorithms and/or statistical analysis techniques that produce an analysis of the second ECG signal having an increased statistical confidence level compared to the analysis generated using the first ECG signal. For instance, in some examples the analyses may use stricter criteria for identifying an arrhythmia condition, may process longer samples of the second ECG data than the samples of first ECG data previously processed, may process more samples of the second ECG data than the samples of the first ECG data previously processed, and/or may process an overall amount of second ECG data that is greater than the amount of first ECG data previously processed. Additionally or alternatively, in an example, reliability is improved by selecting different ECG circuitry (i.e., a sensor and circuitry used for acquiring an ECG signal from a patient) or causing a tighter fit between the second electrode pair and the patient (e.g., by tightening the belt 150 of the ambulatory medical device).

Where the treatment controller refutes or otherwise fails to verify 618 the declared arrhythmia condition, the treatment controller aborts or delays 620 the treatment protocol. In some examples, upon not verifying 618 an arrhythmia condition, the delivery of a therapeutic stimulation pulse is delayed by a predefined time period (e.g., at least 30 seconds, at least 45 seconds, etc.). If via execution of the act 618, or during the delay period, the treatment controller determines that normal sinus rhythm has returned in the patient, the treatment protocol can be aborted, and the medical device can return to a monitoring state via the cardiac monitor. Thus, in these situations, the treatment controller aborts providing any therapeutic stimulation pulse to the patient. Upon aborting or delaying 620 the treatment protocol, the treatment controller returns control to the cardiac monitor, which receives 602 first ECG data, as described above. Alternatively or additionally, in some examples, second ECG signals may also be monitored 614 during the delay or after aborting 620.

However, upon verifying 618 (e.g., prior to, during, after delaying 620 treatment) the arrhythmia declaration, the treatment controller delivers 622, in an attempt to restore a normal rhythm to the patient's heart, one or more therapeutic stimulation pulses as selected in response to the type of arrhythmia condition detected. For example, upon detection by the treatment controller of ventricular fibrillation in the patient, the treatment controller can deliver 622 a defibrillating therapeutic stimulation pulse to the heart of the patient. For example, upon detection by the treatment controller of bradycardia in the patient, the treatment controller can deliver 622 a series of pacing therapeutic stimulation pulses to the heart of the patient. The treatment controller can provide other types of therapeutic stimulation pulses to the patient depending on the arrhythmia condition detected.

After delivery 622 of the therapy, the treatment controller analyzes the first or the second ECG signals to determine 624 whether a "normal" heart rhythm (i.e., not an arrhythmia condition) has been restored. If a normal rhythm has been restored, the treatment controller returns control to the cardiac monitor. However, if a normal rhythm has not been restored, the treatment controller determines whether or not treatment should be continued 626. This determination may be made based on a number of factors, including, for example, whether execution of the treatment protocol has continued for longer than a threshold duration or for more than a threshold number of cycles. Also, this determination may be made based on whether the ambulatory medical device has sufficient resources available to continue execution of the treatment protocol (e.g., whether sufficient battery power remains). If treatment can be continued 626, the treatment protocol may optionally be adjusted 628 to, for example, change the type of therapeutic stimulation pulse provided to the patient (e.g., change from a defibrillation pulse to a pacing pulse) or change the electrical characteristics of a same type of therapeutic stimulation pulse previously provided to the patient (e.g., increase/decrease energy, increase/decrease duration, etc.). If the treatment cannot be continued 626 the monitoring and treatment process 600 ends.

FIG. 6B provides an illustration of a monitoring and treatment protocol 650 (also called a treatment alarm sequence). The treatment protocol 650 may be executed by an ambulatory medical device (e.g., the ambulatory medical device 100). As shown, the protocol 650 includes 7 milestones that occur within 1 minute of abnormality detection. However, the length of the protocol 650 can be longer or shorter depending on certain factors. For example, if the potential arrhythmia rhythm is identified as a VT rhythm, a default response time for the patient may be 60 seconds, which can be adjusted to be in a range of 60 to 180 seconds. For example, if the potential arrhythmia rhythm is identified as a VF rhythm, a default response time may be 25 seconds, which can be adjusted to be in a range of 25 to 60 seconds. Thus, the duration of the protocol 650 can be adjusted to accommodate for these response times. If a treatment alarm sequence is ongoing, in some examples, based on the arrhythmia verification processes described herein the treatment controller can hasten the application of the defibrillation shock so that the shock is delivered sooner than the default of configured time. Otherwise, the treatment controller can delay the shock, for example, an additional 25-45 seconds.

In the example protocol 650, at milestone 1, a cardiac monitor (e.g., the cardiac monitor 214) of the ambulatory medical device declares an arrhythmia based on a first process, an abnormality detection process. At milestone 2, which occurs approximately 5 seconds after milestone 1, the cardiac monitor initiates a treatment protocol and passes control of the ambulatory medical device to a treatment controller (e.g., the treatment controller 216) to complete execution of the treatment protocol. In some examples, as part of initiating the treatment protocol at milestone 2, the cardiac monitor issues an alarm. This alarm may be visual, auditory, or tactile in nature. For example, the alarm may be a siren that continues throughout execution of the treatment protocol.

At milestone 3, which occurs approximately 5 seconds after milestone 2, the treatment controller instructs the mechanism outputting the alarm to increase the alarm's magnitude (e.g., increase the volume of the siren). At milestone 4, which occurs approximately 5 seconds after milestone 3, the treatment controller provides an audio prompt to the patient that instructs the patient to press the response buttons to delay treatment. At milestone 5, which occurs approximately 5 seconds after milestone 4, the treatment controller instructs the gel deployment circuitry to deploy gel. At milestone 6, which occurs approximately 4 seconds after milestone 1, the treatment controller issues an audio prompt to bystanders that instructs the bystanders to not interfere with the treatment protocol. At milestone 7, which occurs approximately 4 seconds after milestone 6, the treatment controller instructs the therapy delivery circuitry to deliver one or more therapeutic stimulation pulses to the patient. As shown in FIG. 6B, the treatment protocol concludes with restoration of a normal sinus rhythm and the treatment controller initiates a monitoring process and passes control of the ambulatory medical device back to the cardiac monitor.

In some examples, the treatment controller verifies the arrhythmia after milestone 5 and before milestone 7, based on one or more second processes, e.g., arrhythmia verification processes. To do so, the treatment controller may execute any of the arrhythmia verification processes described herein.

The abnormality detection and arrhythmia verification processes 604 and 616 can be distinct processes that vary between examples. As such, the abnormality detection and arrhythmia verification processes may include a variety of sub-processes that analyze ECG signals by processing ECG data representative of the ECG signals. For example, the arrhythmia verification process may be an abbreviated version of the abnormality detection process and may include fewer sub-processes than the abnormality detection process in the interest of faster execution. In an example, sub-processes for the abnormality detection process may include one or more of the following sub-processes: a fast Fourier transform (FFT) to analyze ECG signal frequency components; a heart rate analyzer; a spectrum analyzer to analyze patterns within a plurality of ECG signal wavelengths; an ECG morphology analyzer to compare the ECG signal with baseline ECG signals, and various artifact sensors and associated processes to determine whether an ECG signal is artificial (e.g., from poor contact with the skin of the patient). These sub-processes are described in U.S. Pat. No. 5,944,669, titled "Apparatus and Method for Sensing Cardiac Function," which is hereby incorporated herein by reference in its entirety.

In addition, the abnormality detection process and/or the arrhythmia verification process can include one or more confidence sub-processes (e.g., a confidence sub-process implemented by at the cardiac monitor and/or the treatment controller) that determine a confidence level in the declaration of an abnormality or verification of an arrhythmia condition. For example, such a confidence process can be a process for distinguishing a cardiac event from noise in an ECG signal. As an example, such a confidence sub-process may sample portions of the ECG signals in segmented blocks (e.g., one second ECG strips) and determine using, e.g., a machine learning system, whether the samples can be classified as noise or a cardiac event. The confidence process may analyze a portion of the ECG signals, e.g., 10-30 seconds of the received ECG signals, prior to declaring a confidence level in the arrhythmia declaration. In other examples, smaller amounts of ECG signals may be considered in the analysis (e.g., ECG signals acquired over a time period of less than 10 seconds, ECG signal acquired over a time period between 1 and 10 seconds, etc.). Regardless of the amount of ECG data processed by the confidence sub-process, the resulting confidence value may be evaluated by, for example, comparing the value to a threshold value or set of threshold values to determine whether the ECG data represents a cardiac event or noise.

By way of example, if an abnormality is detected by the cardiac monitor in executing one or more of the sub-processes of the abnormality detection process, ECG signals in which the abnormality was detected can be sent to a noise detection process. The noise detection process may be configured to process these ECG signals to determine whether the detected abnormality is an arrhythmia condition or is caused by noise. For example, the output of the noise detection process may be in the form of a flag that is set to indicate whether or not an arrhythmia condition can be declared due to the absence or presence of noise. Additional details regarding the foregoing noise detection process can be found in U.S. Patent Application Publication No. 2016/0000349, titled "SYSTEM AND METHOD FOR DISTINGUISHING A CARDIAC EVENT FROM NOISE IN AN ELECTROCARDIOGRAM (ECG) SIGNAL," which is hereby incorporated herein in by reference its entirety.

Regardless, one or more of these sub-processes (among others identified in U.S. Pat. No. 5,944,669) initially included in the abnormality detection process can be omitted in the arrhythmia verification process. For example, while ECG signals representative of heart rate and heart beat morphology may be analyzed, an FFT of a heart beat pattern may be omitted, thus reducing the time required for the verification analysis. In another example, arrhythmia verification may operate on less ECG data (e.g., based on ECG signals acquired over a time period of between 5 and 10 seconds) than abnormality detection (e.g., based on ECG signals acquired over a time period of between 10 and 50 seconds). One advantage of omitting certain sub-processes is that a second duration of time used to execute the arrhythmia verification process is less than a first duration of time used execute the abnormality detection process. As with other components described herein, instead of or in addition to one of more processors, some or all of the abnormality detection and arrhythmia verification processes may be executed by specialized circuitry (e.g., an ASIC or FPGA).

Table 1 illustrates one example implementation of the abnormality detection and arrhythmia verification processes.

TABLE 1

| Abnormality Detection Process Sub-processes | Abnormality Detection Process Output | Arrhythmia Verification Process Sub-Processes | Arrhythmia Verification Process Output |
|---|---|---|---|
| Fast Fourier transform (FFT) to analyze ECG signal frequency components | Output 1: Declare arrhythmia condition | Execute ECG morphology analyzer to compare the ECG signal with baseline ECG signals | Output 1: Arrhythmia condition verified |
| Execute heart rate analyzer | Output 2: Arrhythmia condition not declared | Execute heart rate analyzer | Output 2: Arrhythmia condition not verified |
| Execute spectrum analyzer to analyze patterns within a plurality of ECG signal wavelengths | | Execute confidence process to confirm that abnormal event is an arrhythmia condition (e.g., VT/VF) | |
| Execute ECG morphology analyzer to compare the ECG signal with baseline ECG signals | | | |
| Execute confidence process to confirm that abnormal event is an arrhythmia condition (e.g., VT/VF) | | | |

TABLE 1-continued

| Abnormality Detection Process Sub-processes | Abnormality Detection Process Output | Arrhythmia Verification Process Sub-Processes | Arrhythmia Verification Process Output |
|---|---|---|---|
| Analyze pulse ox data to determine whether the patient's blood oxygen saturation is above a configurable threshold value, within a configurable range of values, or has deviated from a baseline beyond a threshold value. | | | |
| Analyze respiration data to determine whether the patient's respiration is above a configurable threshold value, within a configurable range of values, or has deviated from a baseline beyond a threshold value. | | | |
| Analyze patient movement data to determine whether the patient's movement is above a configurable threshold value, within a configurable range of values, or has deviated from a baseline beyond a threshold value. | | | |

Examples that include an abnormality detection process and/or an arrhythmia verification process are not limited with regard to the sub-processes included in each process. For instance, in one example, the arrhythmia verification process includes only an FFT to analyze ECG signal frequency components. Alternatively or additionally, other examples may include other sub-processes within either or both of the abnormality detection process and the arrhythmia verification process.

Optionally, as shown in Table 1, the abnormality detection and arrhythmia verification processes may also analyze other data when detecting and verifying. For example, the first or second pair of sensing electrodes (and other pairs of sensing electrodes and multi-function electrodes described herein) may also include at least one of a heart sounds sensor 224 and a tissue fluid monitor 226. The cardiac monitor may access data descriptive of one or more signals acquired by the heart sounds sensor 224 and/or the tissue fluid monitor 226 to further analyze whether the patient is experiencing an arrhythmia condition and determining what type of arrhythmia condition the patient is experiencing.

For instance, in some examples, the first process or the abnormality detection process includes non-ECG based sub-processes as a replacement of, or a supplement to, the ECG based sub-processes described above. For instance, in one example, the abnormality detection process includes one or more of a pulse ox sub-process, a respiration sub-process, and a patient movement sub-process. These sub-processes may be consistently executed as part of the abnormality detection process or may be conditionally executed based on the outcome of the other sub-processes. For instance, in certain examples, the pulse ox, the respiration, and/or the patient movement sub-processes are executed only where the ECG based sub-processes return assessments that are in conflict. In these examples, the pulse ox, the respiration, and/or the patient movement sub-processes may contribute to determining whether an arrhythmia condition is declared by the abnormality detection process. For instance, the abnormality detection process may determine whether an arrhythmia condition is declared using a voting process that includes all of the sub-processes as described further below with reference to FIG. 7.

In certain examples, the pulse ox sub-process analyzes PPG data indicative of the oxygen saturation of the patient's blood to determine whether the patient is experiencing an arrhythmia or other abnormality. This analysis may include comparing the patient's current oxygen saturation level to a previously recorded baseline or to one or more predefined threshold values. For instance, in one example where the pulse ox sub-process compares the patient's current oxygen saturation level to a baseline, the pulse ox sub-process determines that the patient is experiencing an arrhythmia where the patient's current oxygen saturation level deviates from the baseline by 20% or more. The baseline may be configurable between 10% and 90% and therefore may vary between examples. In another example where the pulse ox sub-process compares the patient's current oxygen saturation level to one or more predefined threshold values, the pulse ox sub-process determines that the patient is experiencing an arrhythmia where the patient's current oxygen saturation level transgresses at least one of the threshold values (e.g., 95%). This value may be configurable and therefore may vary between examples.

In some examples, the respiration sub-process analyzes accelerometer data indicative of the patient's respiration rate to determine whether the patient is experiencing an arrhythmia or other abnormality. This analysis may include comparing the patient's current respiration rate to a previously recorded baseline or to one or more predefined threshold values. For instance, in one example where the respiration sub-process compares the patient's current respiration rate to a baseline, the respiration sub-process determines that the patient is experiencing an arrhythmia where the patient's current respiration rate deviates from the baseline by 10% or more. The baseline may be configurable between 10% and 90% and therefore may vary between examples. In another example where the respiration sub-process compares the patient's current respiration rate to one or more predefined threshold values, the respiration sub-process determines that the patient is experiencing an arrhythmia where the patient's current respiration rate transgresses at least one of the threshold values (e.g., 12 or 25 breaths per minute). This value may be configurable and therefore may vary between examples.

In some examples, the movement sub-process analyzes accelerometer data indicative of the patient's movement to determine whether the patient is experiencing an arrhythmia or other abnormality. This analysis may include comparing the patient's current movement to a previously recorded baseline or to one or more predefined threshold values. For instance, in one example where the movement sub-process compares the patient's current movement to a baseline, the movement sub-process determines that the patient is experiencing an arrhythmia where the patient's current movement rate deviates from the baseline by 30% or more. The baseline may be configurable between 10% and 90% and therefore may vary between examples. In another example where the movement sub-process compares the patient's current movement to one or more predefined threshold values, the movement sub-process determines that the patient is experiencing an arrhythmia where the patient's current movement rate transgresses at least one of the threshold values (e.g., substantially no movement). This value may be configurable and therefore may vary between examples. One example of the movement sub-process used to supplement ECG based arrhythmia detection processes is described in U.S. Pat. No. 7,974,689, titled "Wearable Medical Treatment Device with Motion/Position Detection," which is hereby incorporated herein by reference in its entirety. The movement sub-process described in U.S. Pat. No. 7,974,689 determines whether the patient is exhibiting substantial movement and uses that determination to inform its ultimate determination as to whether the patient is experiencing an arrhythmia.

The arrhythmia detection process is designed to evaluate several rate inputs simultaneously to determine the patient's heart rate. The arrhythmia detection process uses two QRS detector sub-processes, one to an electrode pair, to provide independent assessments of heart rate. ECG signal frequencies are also analyzed using an FFT sub-process, which decomposes an analog waveform into its frequency components and allows input signal analysis in the frequency domain. The FFT sub-process output is analyzed to determine the strongest frequency component indicative of heart rate. The FFT analysis often provides the best indication of heart rate, specifically during ventricular tachycardia (VT) or ventricular fibrillation (VF). Finally, a morphology analysis sub-process is also used to determine the heart rate.

The arrhythmia detection process then applies logical weights based on comparing leads, signal quality, and historic rate values in order to determine the best inputs to accurately monitor the patient's heart rate. For example, if the heart rate from the two QRS detector sub-processes do not match, less weight is applied to these inputs and greater weight is applied to other sources.

Once the arrhythmia detection process determines the best combination of factors to assess heart rate, the heart rate is then categorized as below the VT threshold, above the VT threshold but below the VF threshold, or above the VF threshold. These thresholds are programmed for the patient during setup. If the rate exceeds the VT or the VF threshold, the arrhythmia detection process then proceeds to a morphology analysis sub-process comparing the patient's normal rhythm baseline template obtained during device setup to the current QRS morphology.

The arrhythmia detection process also applies a confidence sub-process as part of the process for deciding to treat or not to treat an arrhythmia. The confidence sub-process is the sum of the individually weighted input factors of heart rate, morphology, response button use, and signal quality. The input factors can contribute positively or negatively to the confidence. If an input factor is deemed unreliable, its weight can be lessened or redistributed entirely to other factors.

Once an arrhythmia is declared, the confidence sub-process must decide if the rhythm is treatable based on the duration or persistence of the arrhythmia. If a value of confidence generated by the confidence sub-process falls below a specified level, the treatment protocol is terminated and the system reverts to monitoring for a new arrhythmia.

For example, if a patient uses the response buttons after hearing the alarms and the heart rate slows, the confidence value would decrease. If the patient releases the response buttons and the heart rate increases or becomes abnormal, the confidence value would increase. Any one and/or all of the sub-processes defined by the arrhythmia detection process can be used within either or both of the abnormality detection and arrhythmia verification processes.

In some examples, the abnormality detection process and/or the arrhythmia verification process are each voting processes that make determinations based on a summary of the sub-processes they execute. Further the abnormality detection process and/or the arrhythmia verification process may be configuration data driven processes that reference configuration data parameters which specify sub-processes to execute. FIG. 7 illustrates one example of a voting process 700 that is configuration data driven and that, therefore, can be used to implement the abnormality detection process or arrhythmia verification process.

Figure 7:
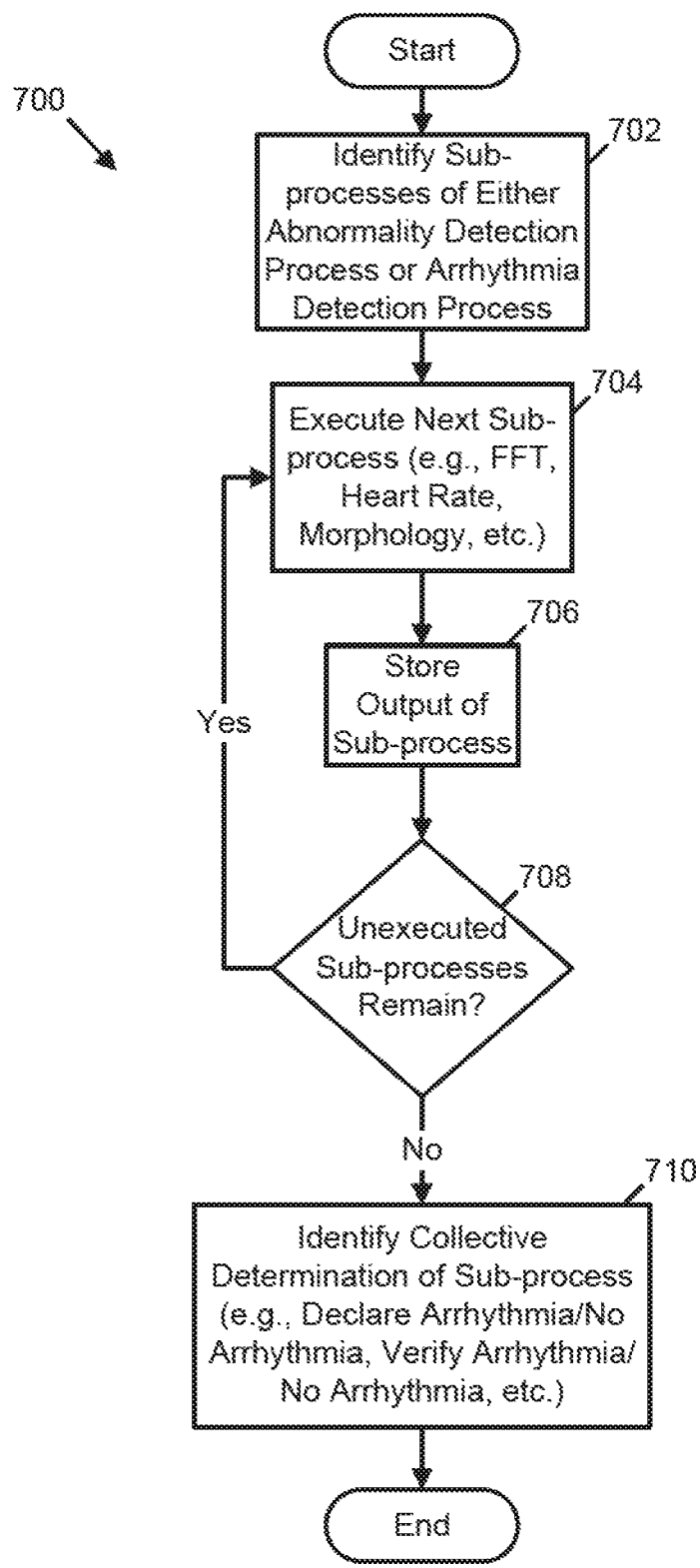
FIG. 7 depicts a configurable voting process in accordance with at least one example disclosed herein.

As shown in FIG. 7, the voting process 700 starts in act 702 with a voting controller (e.g., either the cardiac monitor or the treatment controller) identifying, within configuration data, a list of one or more sub-processes to execute as part of the voting process 700. This configuration data may be stored, for example, in the data storage 204 of the medical device controller 120. The list of sub-processes may include any of the sub-processes listed in Table 1 above or elsewhere in this disclosure. In some examples, in addition to storing identifiers of the sub-processes to include in the voting process 700, the configuration data also stores weights to be applied to the output (or "vote") of each sub-process and one or more threshold values used to judge the overall outcome of the voting process.

In act 704, voting controller executes the next unexecuted sub-process from the list of one or more sub-processes generated in the act 702. In act 706, the voting controller stores the result of the sub-process executed in the act 704. In act 708, the voting controller determines whether any unexecuted sub-processes remain on the list of one or more sub-processes generated in the act 702. If so, the voting controller returns to the act 702. If no unexecuted sub-processes remain, in act 710 the voting controller identifies the collective determination of the sub-processes using the one or more threshold values stored in the configuration information and the voting process 700 ends.

To increase speed and decrease configurability, other examples implement the abnormality detection process and/or the arrhythmia verification process to include a fixed set of sub-processes. FIG. 8 illustrates an abnormality detection process 800 as implemented in these examples. FIG. 9 illustrates an arrhythmia verification process 900 as implemented in these examples.

Figures 8, 9:
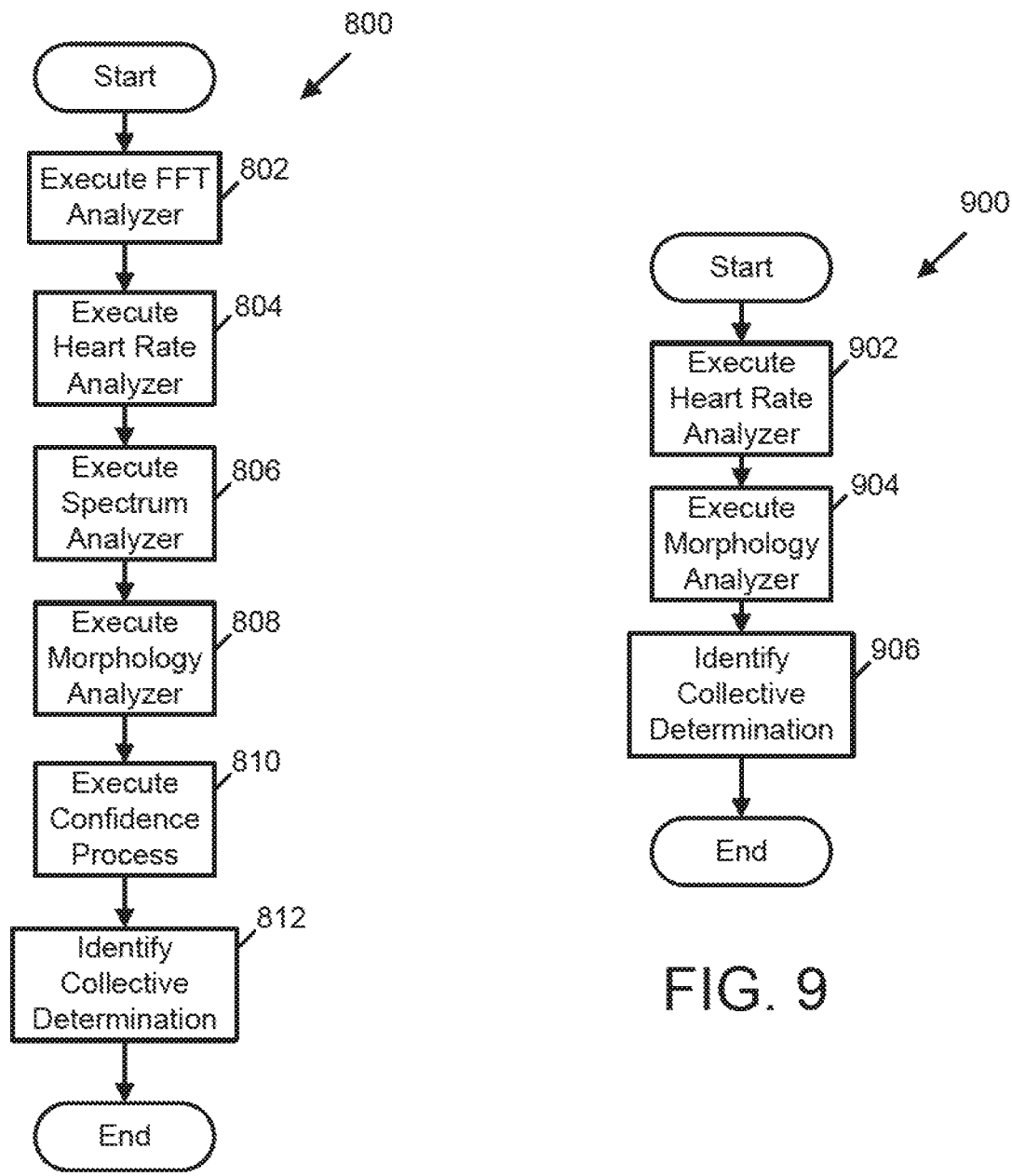
FIG. 8 depicts an abnormality detection process in accordance with at least one example disclosed herein.
FIG. 9 depicts an arrhythmia verification process in accordance with at least one example disclosed herein.

As shown in FIG. 8, the abnormality detection process 800 starts in act 802 with the cardiac monitor executing an FFT analyzer that generates an FFT of the first ECG data to compare frequency components to a baseline for the patient to determine whether the patient is suffering from an arrhythmia condition. In act 804, the cardiac monitor executes a heart rate analyzer to compare the patient's heart rate to a baseline for the patient to determine whether the patient is suffering from an arrhythmia condition. In act 806, the cardiac monitor executes a spectrum analyzer to determine whether patterns within a plurality of wavelengths indicate that the patient is suffering from an arrhythmia condition. In act 808, the cardiac monitor executes a morphology analyzer to compare the morphology indicated by the first ECG data to a benchmark established for the patient to determine whether the patient is suffering from an arrhythmia condition. In act 810, the cardiac monitor executes a confidence process to establish an overall confidence that the detected abnormal event is an arrhythmia condition (and not, for example, noise). In act 812, the cardiac monitor identifies the collective determination of the sub-processes executed in acts 802-810 and the abnormality detection process 800 ends. In some examples, the determination of the act 812 is made by summarizing the output of the sub-processes (e.g., summing their return values) and comparing the summary to one or more threshold values.

As shown in FIG. 9, the arrhythmia verification process 900 starts in act 902 with the treatment controller executing a heart rate analyzer to compare the patient's heart rate to a baseline for the patient to determine whether the patient is suffering from an arrhythmia condition. In act 904, the treatment controller executes a morphology analyzer to compare the morphology indicated by the first ECG data to a benchmark established for the patient to determine whether the patient is suffering from an arrhythmia condition. In act 906, the treatment controller identifies the collective determination of the sub-processes executed in acts 902 and 904 and the arrhythmia verification process 900 ends. In some examples, the determination of the act 906 is made by summarizing the output of the sub-processes (e.g., summing their return values) and comparing the summary to one or more threshold values.

As described above, in some examples, the abnormality detection process and the arrhythmia verification process execute different sets of sub-processes. However, in other examples, the abnormality detection process and the arrhythmia verification process execute a common set of sub-processes. Thus, the examples described herein are not limited to abnormality detection or arrhythmia verification processes that execute different or common sets of sub-processes. Nor are the examples described herein limited to a specific set of sub-processes.

Example Configurations

Some examples advantageously leverage the features disclosed above to provide for an ambulatory medical treatment device that utilizes distinct sensing electrodes in execution of abnormality detection and arrhythmia verification processes. Examples of this ambulatory medical treatment device and the processes it executes are illustrated by FIGS. 10 and 11.

Figure 10:
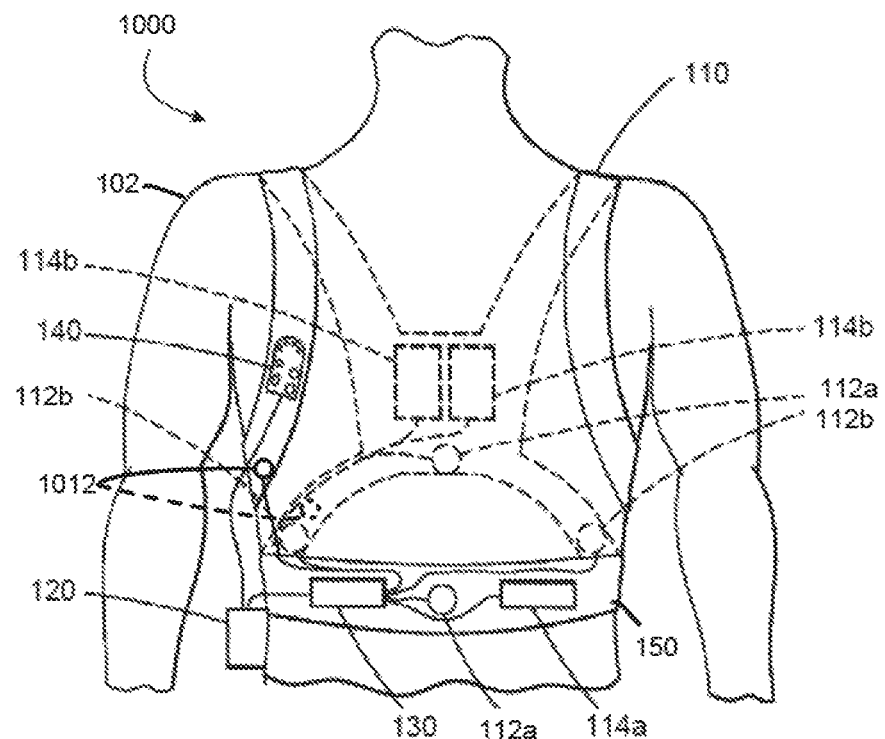
FIG. 10 depicts another wearable, ambulatory, external medical device in accordance with at least one example disclosed herein.
Figure 11:
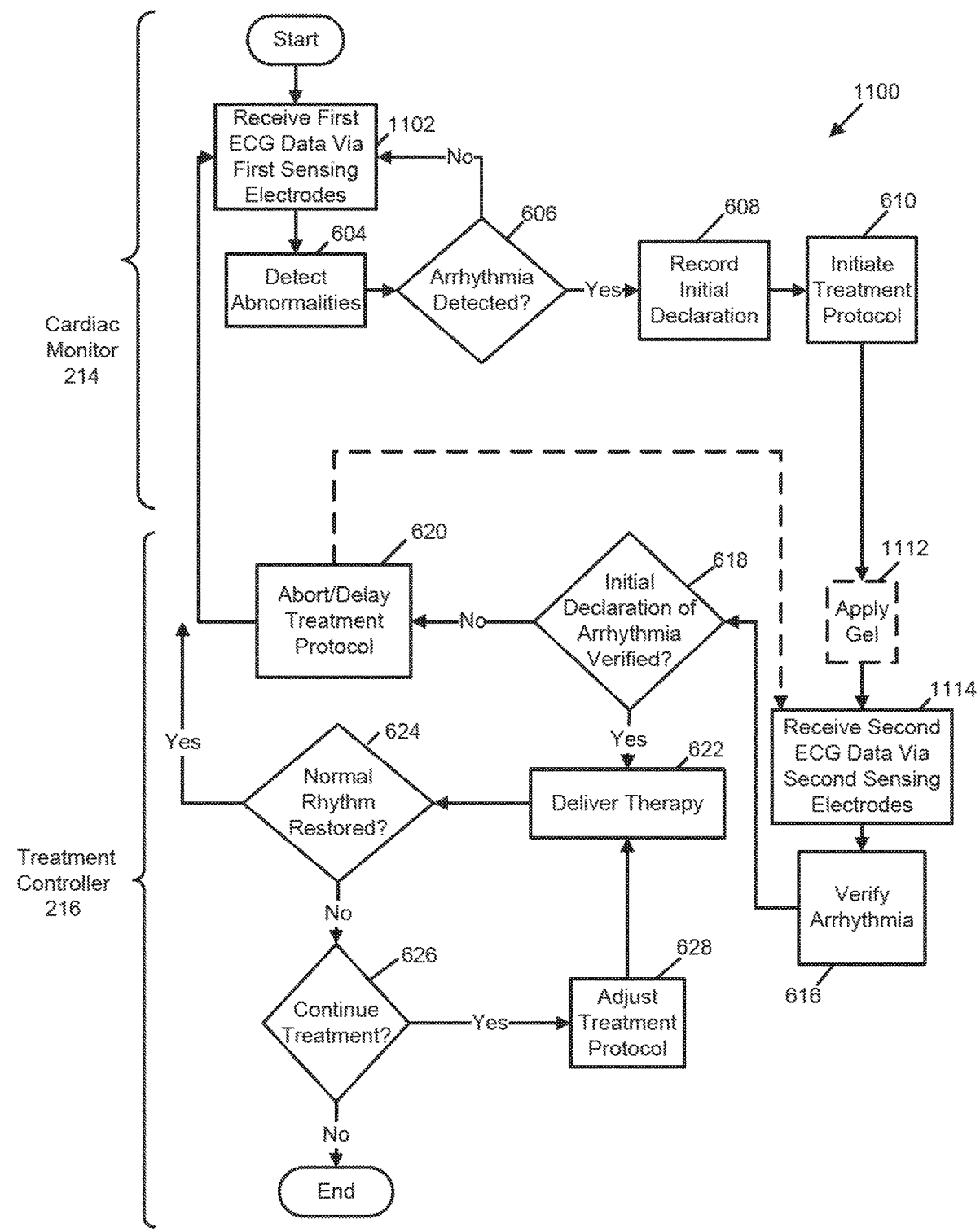
FIG. 11 depicts another monitoring and treatment process including arrhythmia verification in accordance with at least one example disclosed herein.

As shown, FIG. 10 includes a medical device 1000 that is external, ambulatory, and wearable by the patient 102. The medical device 1000 includes many of the components of the medical device 100 described above. For example, the medical device 1000 includes the garment 110, the sensing electrode pairs 112, the therapy electrode pair 114, the medical device controller 120, the connection pod 130, the patient interface pod 140, and the belt 150. The therapy electrode pair 114 is configured to couple externally to a skin of the patient 102 and to provide one or more therapeutic stimulation pulses to a heart of the patient 102 during execution of a treatment protocol.

In addition, the medical device 1000 includes a distinct sensing electrode pair 1012 that is configured to couple externally to the skin of the patient 102 and to acquire ECG signals. In some examples, this distinct pair of electrodes 1012 includes conductive electrodes. However, any one of the electrodes of the pair of electrodes 1012 may be any of the conductive electrodes or dry electrodes described herein.

In some examples, the medical device 1000 is configured to acquire first ECG signals via the electrode pairs 112 and to acquire second ECG signals via the pair of electrodes 1012. In these examples, second ECG data based on the second ECG signals has an improved reliability over first ECG data based on the first ECG signals.

In some examples, the medical device controller 120 of the medical device 1000 includes a cardiac monitor (e.g., the cardiac monitor 214) and a treatment controller (e.g., the treatment controller 216). In these examples, the cardiac monitor and treatment controller are configured to execute monitoring and treatment processes that include abnormality detection and arrhythmia verification processes. At least one example monitoring and treatment process 1100 that the cardiac monitor and the treatment controller are configured to execute is described further below with reference to FIG. 11.

As shown in FIG. 11, the monitoring and treatment process 1100 includes the actions of the monitoring and treatment process 600. However, many of the details of the monitoring and treatment process 600 are omitted from the following description of the monitoring and treatment process 1100 for the sake of brevity. As shown in FIG. 11, the monitoring and treatment process 1100 starts with the cardiac monitor receiving 1102 first ECG data based on first ECG signals acquired by at least one first pair of sensing electrodes. In this example, the at least one first pair of sensing electrodes includes the sensing electrode pairs 112. In some examples, the act of receiving 1102 the first ECG data includes one or more of the acts described above with reference to the act 602.

Next, the cardiac monitor attempts to detect abnormalities 604 in the first ECG data by executing an abnormality detection process as described above. Where the cardiac monitor does not detect 606 an arrhythmia condition of the patient, the cardiac monitor returns to receiving 1102 first ECG data. However, upon detecting 606 that the patient is experiencing an arrhythmia condition, the cardiac monitor records 608 an initial arrhythmia declaration and initiates 610 a treatment protocol.

In one example, after initiation 610 of the treatment protocol, the treatment controller controls, via a gel dispenser and associated circuitry, optional application 1112 of conductive gel between the patient's skin and a second pair of electrodes (e.g., the electrode pair 1012). The conductive gel may be applied between the second pair of electrodes and the skin of the patient prior to acquiring second ECG signals, as described herein. In some examples, the act of applying 1112 the conductive gel includes one or more of the acts described above with reference to the act 612.

Regardless of whether gel is applied 1112, the monitoring and treatment process 1100 continues with the treatment controller receiving 1114 second ECG data based on second ECG signals acquired by the second pair of electrodes. In this example, the second pair of electrodes is the pair of sensing electrodes 1012. Where this second pair of electrodes is used, the second ECG signals (and resulting data) benefit from increased reliability due to increased accuracy and precision of conductive sensing electrodes. In some examples, the act of receiving 1114 the second ECG data includes one or more of the acts described above with reference to the act 614.

Next, the treatment controller attempts to verify 616 the declared arrhythmia using the second ECG data by executing an arrhythmia verification process. In an example, the verification 616 of the second ECG data results in a more reliable determination of whether or not the patient is experiencing an arrhythmia condition.

Where the treatment controller fails to verify 618 the declared arrhythmia condition, the treatment controller aborts or delays 620 the treatment protocol. Upon verifying 618 the arrhythmia declaration, the treatment controller delivers 622, in an attempt to restore a normal rhythm to the patient's heart, one or more therapeutic stimulation pulses as selected in response to the type of arrhythmia condition detected. This verification 618 may occur during a period of time in which treatment has been delayed 620 or may occur prior to any delay 620 of treatment.

After delivery 622 of the therapy, the treatment controller analyzes the second ECG signals to determine 624 whether a "normal" heart rhythm (i.e., not an arrhythmia condition) has been restored. If a normal rhythm has been restored, the treatment controller returns control to the cardiac monitor. However, if a normal rhythm has not been restored, the treatment controller determines whether or not treatment should be continued 626. If treatment can be continued 626, the treatment protocol may optionally be adjusted 628 to, for example, change the type of therapeutic stimulation pulse provided to the patient. If the treatment cannot be continued 626, the monitoring and treatment process 1100 ends.

Some examples advantageously leverage the features disclosed above to provide for an ambulatory medical treatment device that utilizes one or more pairs of sensing electrodes in execution of an abnormality detection process and one or more pairs of multi-function electrodes in execution of an arrhythmia verification process. Examples of this ambulatory medical treatment device and the processes it executes are illustrated by FIGS. 12 and 13.

Figure 12:
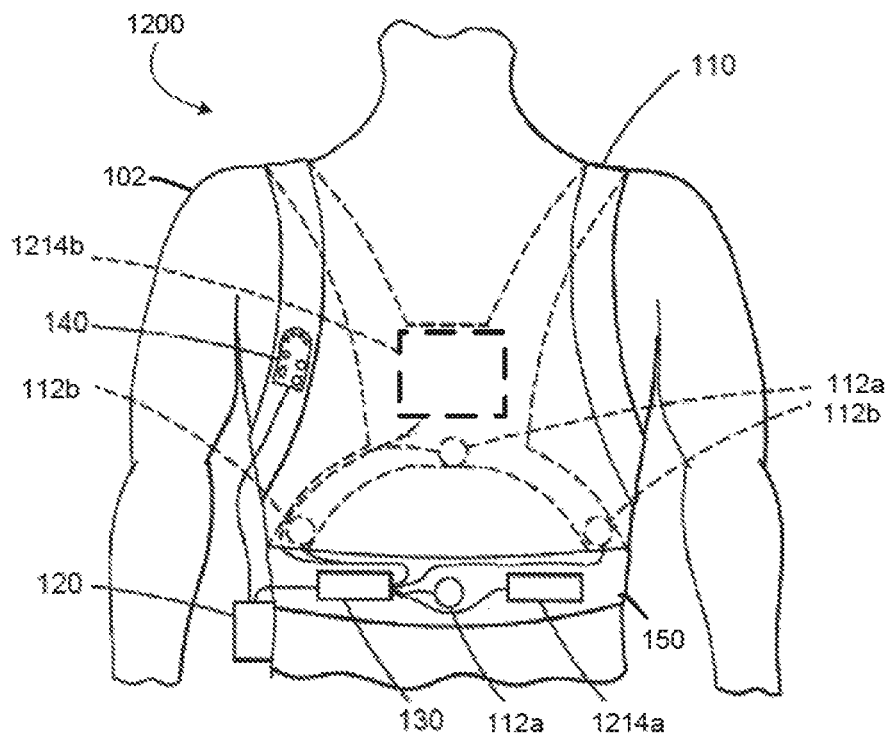
FIG. 12 depicts another wearable, ambulatory, external medical device in accordance with at least one example disclosed herein.
Figure 13:
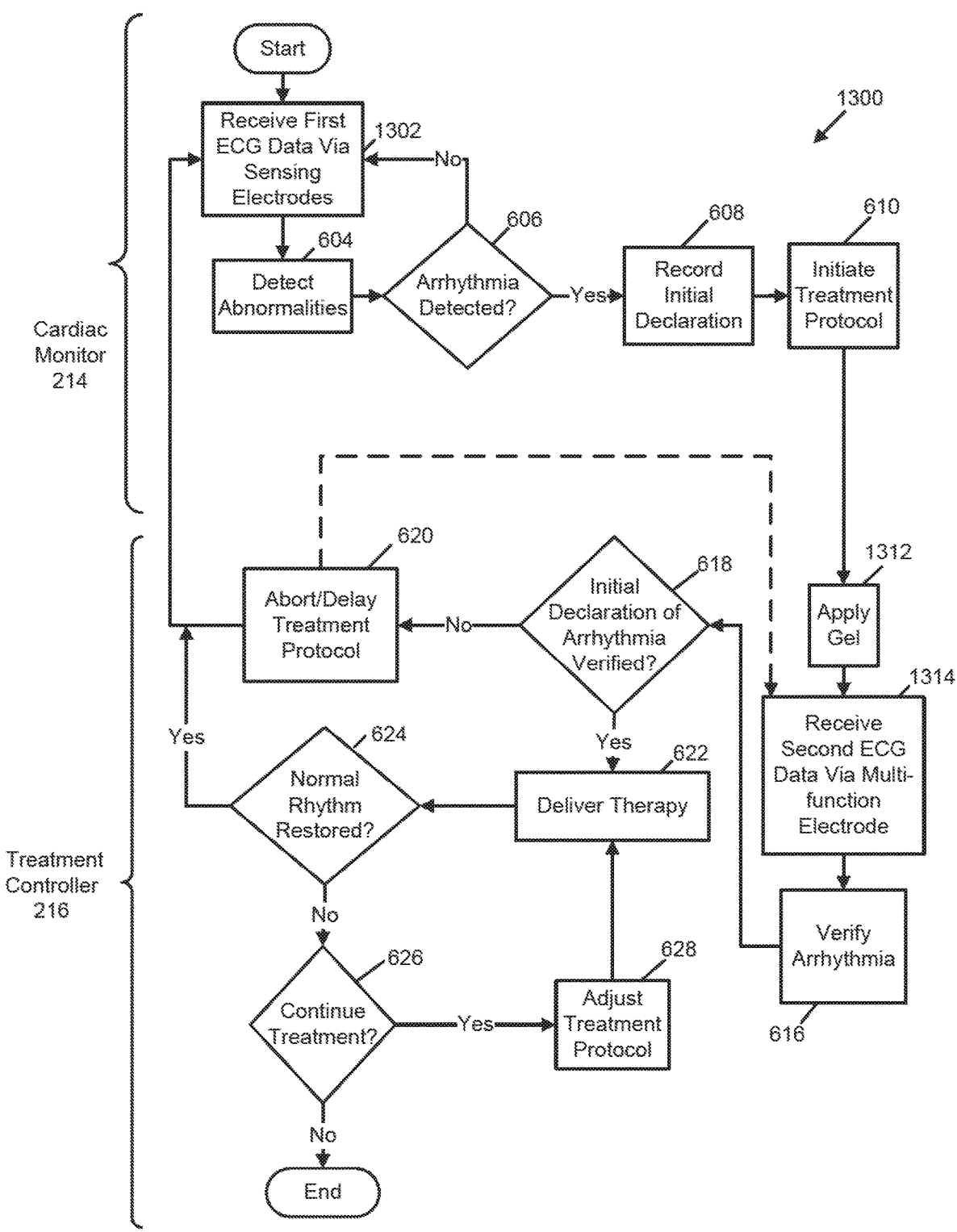
FIG. 13 depicts another monitoring and treatment process including arrhythmia verification in accordance with at least one example disclosed herein.

As shown, FIG. 12 includes a medical device 1200 that is external, ambulatory, and wearable by the patient 102. The medical device 1200 includes many of the components of the medical device 100 described above. For example, the medical device 1200 includes the garment 110, the sensing electrode pairs 112, the medical device controller 120, the connection pod 130, the patient interface pod 140, and the belt 150. The sensing electrode pairs 112 are configured to couple externally to a skin of a patient and to acquire first ECG signals to detect an arrhythmia condition of the patient 102.

In addition, the medical device 1200 includes a pair of multi-function electrodes 1214 comprising multi-function electrodes 1214a and 1214b. Each multi-function electrode 1214a and 1214b of the multi-function electrode pair 1214 is configured to couple externally to the skin of the patient 102, to provide one or more therapeutic stimulation pulses to the heart of the patient 102 during execution of a treatment protocol, and to acquire second ECG signals to verify the arrhythmia condition of the patient 102. In some examples, each multi-function electrode 1214a and 1214b of the multi-function electrode pair 1214 includes a therapy electrode and a conductive sensing electrode. In some examples, the therapy electrode and the sensing electrode are switched between sensing and therapy circuitry included in the medical device 1200 to implement sensing and therapy modes and functionality. In some examples, each multi-function electrode 1214a and 1214b of the multi-function electrode pair 1214 includes a multi-function electrode 402. In some examples, each multi-function electrode 1214a and 1214b of the multi-function electrode pair 1214 is disposed within a therapy pad, such as the therapy pad 500 illustrated in FIG. 5 above or as described above with reference to FIG. 1.

In some examples, the medical device 1200 is configured to acquire first ECG signals via the sensing electrode pair 112 and to acquire second ECG signals via the multi-function electrode pair 1214. In these examples, second ECG data based on the second ECG signals has an improved reliability over first ECG data based on the first ECG signals.

In some examples, the medical device controller 120 of the medical device 1200 includes a cardiac monitor (e.g., the cardiac monitor 214) and a treatment controller (e.g., the treatment controller 216). In these examples, the cardiac monitor and treatment controller are configured to execute monitoring and treatment processes that include abnormality detection and arrhythmia verification processes. At least one example monitoring and treatment process 1300 that the cardiac monitor and the treatment controller are configured to execute is described further below with reference to FIG. 13.

As shown in FIG. 13, the monitoring and treatment process 1300 includes the actions of the monitoring and treatment process 600. However, many of the details of the monitoring and treatment process 600 are omitted from the following description of the monitoring and treatment process 1300 for the sake of brevity. As shown in FIG. 13, the monitoring and treatment process 1300 starts with the cardiac monitor receiving 1302 first ECG data based on first ECG signals acquired by sensing electrodes. In this example, these sensing electrodes include the electrode pairs 112. In some examples, the act of receiving 1302 the first ECG data includes one or more of the acts described above with reference to the act 602.

Next, the cardiac monitor attempts to detect abnormalities 604 in the first ECG data by executing an abnormality detection process as described above. Where the cardiac monitor does not detect 606 an arrhythmia condition of the patient, the cardiac monitor returns to receiving 1302 first ECG data. However, upon detecting 606 that the patient is experiencing an arrhythmia condition, the cardiac monitor records 608 an initial arrhythmia declaration and initiates 610 a treatment protocol.

In one example, after initiation 610 of the treatment protocol, the treatment controller controls, via a gel dispenser and associated circuitry, application 1312 of conductive gel between the patient's skin and a second pair of electrodes (e.g., the multi-function electrode pair 1214). The conductive gel may be applied between the second pair of electrodes and the skin of the patient prior to acquiring second ECG signals, as described herein. In some examples, the act of applying 1312 the conductive gel includes one or more of the acts described above with reference to the act 612.

Regardless of whether gel is applied 1312, the monitoring and treatment process 1300 continues with the treatment controller receiving 1314 second ECG data based on second ECG signals acquired by the second pair of electrodes. In this example, the second pair of electrodes is the pair of multi-function electrodes 1214. Where this second pair of electrodes is used, the second ECG signals (and resulting data) benefit from increased reliability due to increased accuracy and precision of conductive electrodes. In some examples, the act of receiving 1314 the second ECG data includes one or more of the acts described above with reference to the act 614.

Next, the treatment controller attempts to verify 616 the declared arrhythmia using the second ECG data by executing an arrhythmia verification process. In an example, the verification 616 of the second ECG data results in a more reliable determination of whether or not the patient is experiencing an arrhythmia condition.

Where the treatment controller refutes or otherwise fails to verify 618 the declared arrhythmia condition, the treatment controller aborts or delays 620 the treatment protocol. Upon verifying 618 the arrhythmia declaration, the treatment controller delivers 622, in an attempt to restore a normal rhythm to the patient's heart, one or more therapeutic stimulation pulses as selected in response to the type of arrhythmia condition detected. This verification 618 may occur during a period of time in which treatment has been delayed 620 or may occur prior to any delay 620 of treatment.

After delivery 622 of the therapy, the treatment controller analyzes the second ECG signals to determine 624 whether a "normal" heart rhythm (e.g., normal sinus rhythm) has been restored. If a normal rhythm has been restored, the treatment controller returns control to the cardiac monitor. However, if a normal rhythm has not been restored, the treatment controller determines whether or not treatment should be continued 626. If treatment can be continued 626, the treatment protocol may optionally be adjusted 628 to, for example, change the type of therapeutic stimulation pulse provided to the patient. If the treatment cannot be continued 626, the monitoring and treatment process 1300 ends.

Some examples advantageously leverage the features disclosed above to provide for an ambulatory medical treatment device that utilizes distinct pairs of sensing electrodes and gel deployment in execution of abnormality detection and arrhythmia verification processes. Examples of this ambulatory medical treatment device and the processes it executes are illustrated by FIGS. 14 and 15.

Figure 14:
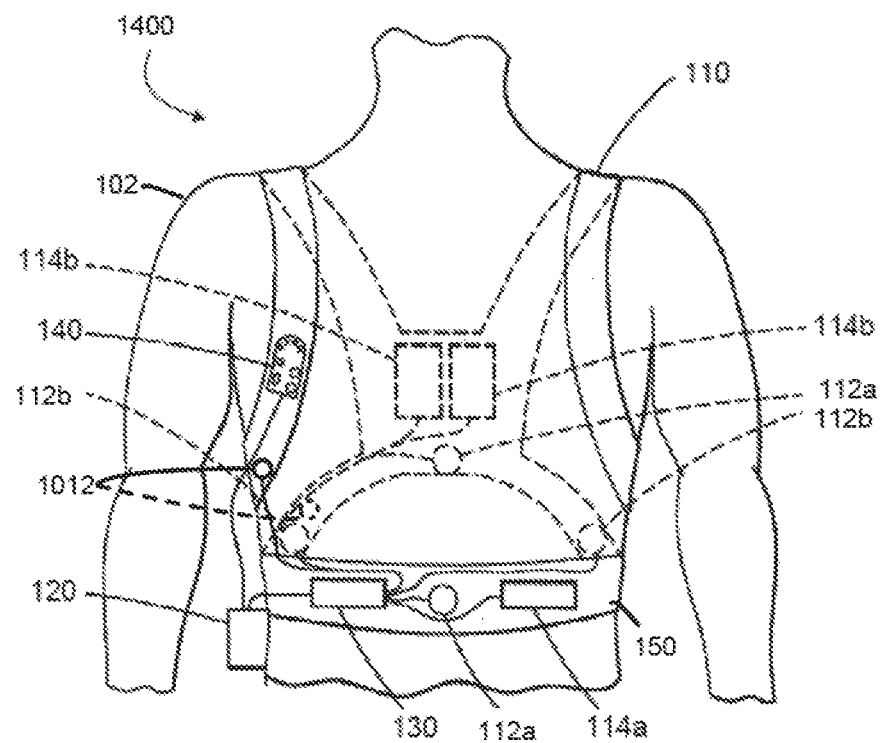
FIG. 14 depicts another wearable, ambulatory, external medical device in accordance with at least one example disclosed herein.
Figure 15:
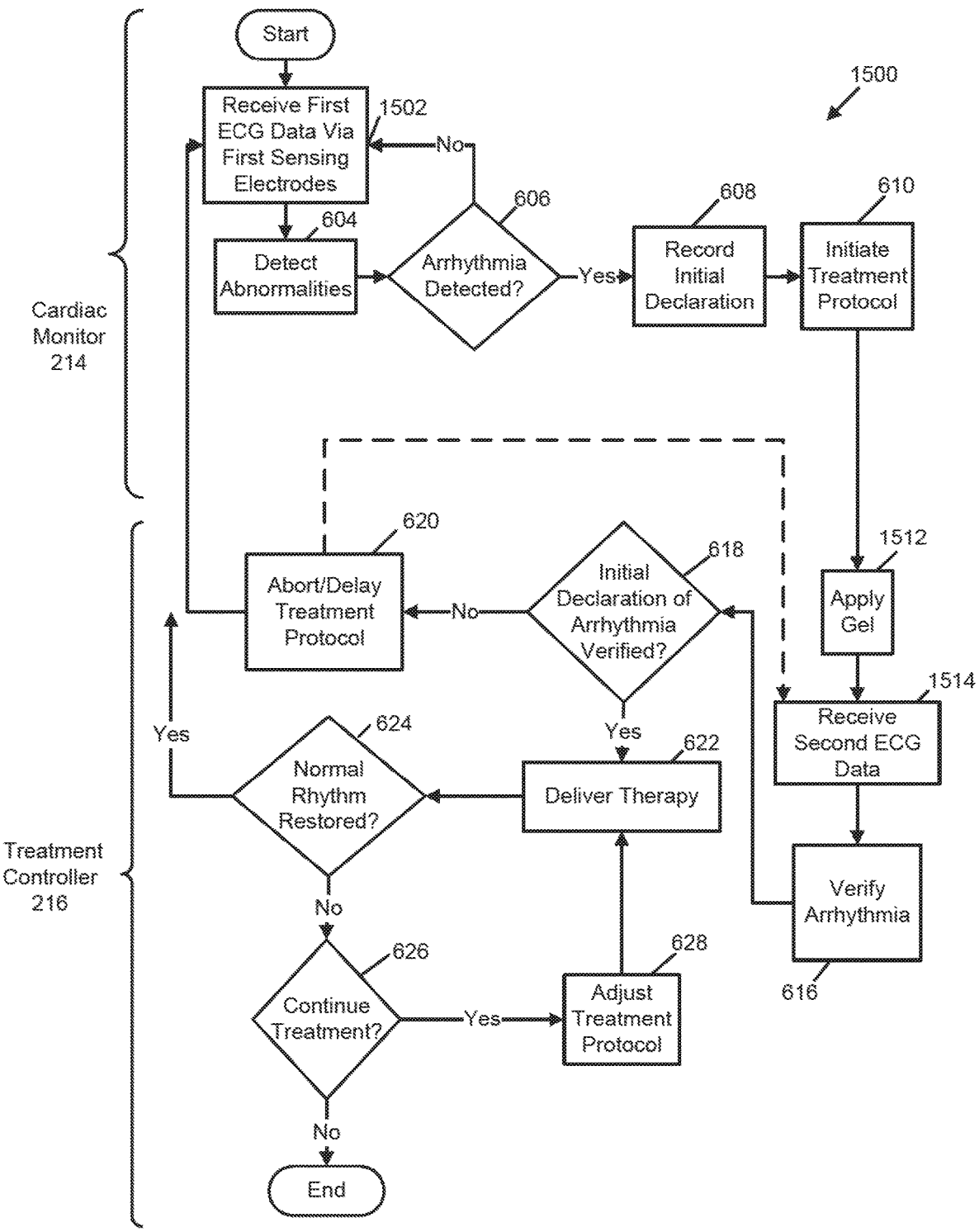
FIG. 15 depicts another monitoring and treatment process including arrhythmia verification in accordance with at least one example disclosed herein.

As shown, FIG. 14 includes a medical device 1400 that is external, ambulatory, and wearable by the patient 102. The medical device 1400 includes the components of the medical device 100 described above. For example, the medical device 1400 includes the garment 110, the therapy electrode pair 114, two pairs of sensing electrodes 112a and 112b, the medical device controller 120, the connection pod 130, the patient interface pod 140, and the belt 150. Each of the electrodes is configured to couple externally to a skin of the patient 102. The therapy electrode pair 114 is also configured to provide one or more therapeutic stimulation pulses to a heart of the patient 102 during execution of a treatment protocol. The therapy electrodes 114 are included within therapy pads that also house gel dispensers coupled to and under control of gel dispenser circuitry. This gel dispenser circuitry is coupled to and under control of a processor within the medical device controller 120. In addition, the medical device 1400 includes the distinct sensing electrode pair 1012 described above with reference to FIG. 10.

In some examples, the medical device 1400 is configured to acquire first ECG signals via the sensing electrode pairs 112 and to acquire second ECG signals via the sensing electrode pair 1012. The sensing electrode pairs 112 may include, for example, dry electrodes. The sensing electrode pair 1012 may include, for example, conductive electrodes. In some examples, second ECG data based on the second ECG signals has an improved reliability over first ECG data based on the first ECG signals.

In some examples, the medical device controller 120 of the medical device 1400 includes a cardiac monitor (e.g., the cardiac monitor 214) and a treatment controller (e.g., the treatment controller 216). In these examples, the cardiac monitor and treatment controller are configured to execute monitoring and treatment processes that include abnormality detection and arrhythmia verification processes. At least one example monitoring and treatment process 1500 that the cardiac monitor and the treatment controller are configured to execute is described further below with reference to FIG. 15.

As shown in FIG. 15, the monitoring and treatment process 1500 includes the actions of the monitoring and treatment process 600. However, many of the details of the monitoring and treatment process 600 are omitted from the following description of the monitoring and treatment process 1500 for the sake of brevity. As shown in FIG. 15, the monitoring and treatment process 1500 starts with the cardiac monitor receiving 1502 first ECG data based on first ECG signals acquired by at least one first pair of sensing electrodes. In this example, the at least one first pair of sensing electrodes includes the sensing electrode pairs 112. In some examples, the act of receiving 1502 the first ECG data includes one or more of the acts described above with reference to the act 602.

Next, the cardiac monitor attempts to detect abnormalities 604 in the first ECG data by executing an abnormality detection process as described above. Where the cardiac monitor does not detect 606 an arrhythmia condition of the patient, the cardiac monitor returns to receiving 1502 first ECG data. However, upon detecting 606 that the patient is experiencing an arrhythmia condition, the cardiac monitor records 608 an initial arrhythmia declaration and initiates 610 a treatment protocol.

In one example, after initiation 610 of the treatment protocol, the treatment controller controls, via a gel dispenser and associated circuitry, application 1512 of conductive gel between the patient's skin and a second pair of electrodes (e.g., the electrode pair 1012). The conductive gel may be applied between the second pair of electrodes and the skin of the patient prior to acquiring second ECG signals, as described herein. In some examples, the act of applying 1512 the conductive gel includes one or more of the acts described above with reference to the act 612.

The monitoring and treatment process 1500 continues with the treatment controller receiving 1514 second ECG data based on second ECG signals acquired by the second pair of electrodes. In this example, the second pair of electrodes is the pair of sensing electrodes 1012. Where this second pair of electrodes is used, the second ECG signals (and resulting data) benefit from increased reliability due to increased accuracy and precision of conductive sensing electrodes. In some examples, the act of receiving 1514 the second ECG data includes one or more of the acts described above with reference to the act 614.

Next, the treatment controller attempts to verify 616 the declared arrhythmia using the second ECG data by executing an arrhythmia verification process. In an example, the verification 616 of the second ECG data results in a more reliable determination of whether or not the patient is experiencing an arrhythmia condition.

Where the treatment controller refutes or otherwise fails to verify 618 the declared arrhythmia condition, the treatment controller aborts or delays 620 the treatment protocol. Upon verifying 618 the arrhythmia declaration, the treatment controller delivers 622, in an attempt to restore a normal rhythm to the patient's heart, one or more therapeutic stimulation pulses as selected in response to the type of arrhythmia condition detected. This verification 618 may occur during a period of time in which treatment has been delayed 620 or may occur prior to any delay 620 of treatment.

After delivery 622 of the therapy, the treatment controller analyzes the second ECG signals to determine 624 whether a "normal" heart rhythm (i.e., not an arrhythmia condition) has been restored. If a normal rhythm has been restored, the treatment controller returns control to the cardiac monitor. However, if a normal rhythm has not been restored, the treatment controller determines whether or not treatment should be continued 626. If treatment can be continued 626, the treatment protocol may optionally be adjusted 628 to, for example, change the type of therapeutic stimulation pulse provided to the patient. If the treatment cannot be continued 626, the monitoring and treatment process 1500 ends.

Some examples advantageously leverage the features disclosed above to provide for an ambulatory medical treatment device that executes distinct abnormality detection and arrhythmia verification processes. Examples of these ambulatory medical treatment devices and the processes they execute are illustrated by FIGS. 16-19.

Figure 16:
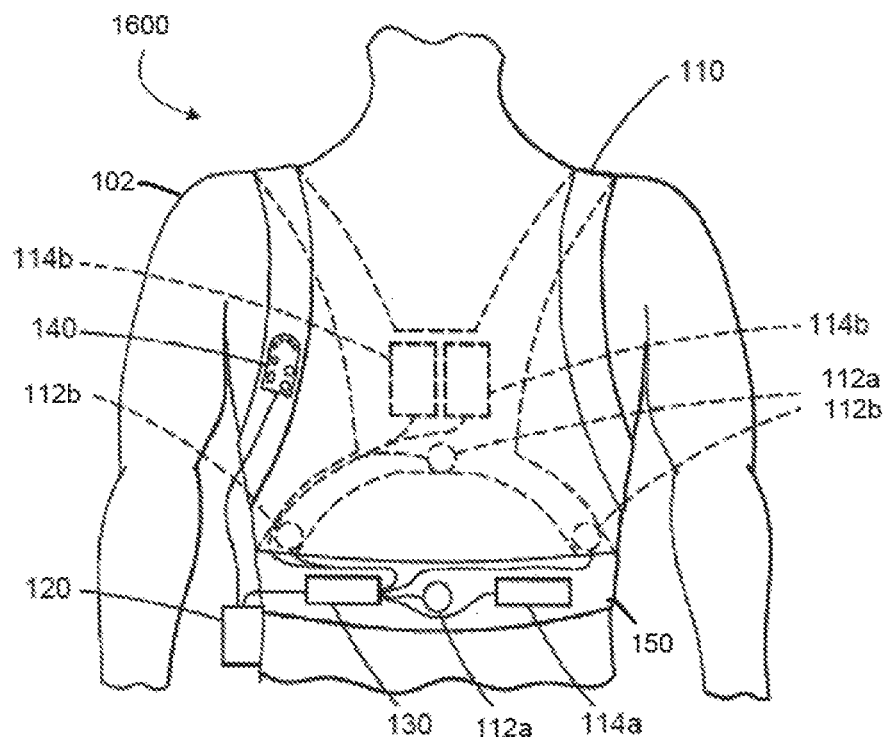
FIG. 16 depicts another wearable, ambulatory, external medical device in accordance with at least one example disclosed herein.

As shown, FIG. 16 includes a medical device 1600 that is external, ambulatory, and wearable by the patient 102. The medical device 1600 includes many of the components of the medical device 100 described above. For example, the medical device 1600 includes the garment 110, the therapy electrode pair 114, the pairs of sensing electrodes 112, the medical device controller 120, the connection pod 130, the patient interface pod 140, and the belt 150. Each of the electrodes is configured to couple externally to a skin of the patient 102. The therapy electrode pair 114 is also configured to provide one or more therapeutic stimulation pulses to a heart of the patient 102 during execution of a treatment protocol. The sensing electrode pairs 112 are configured to couple externally to a skin of a patient and to acquire ECG signals of the patient 102.

In some examples, the medical device 1600 is configured to acquire first and second ECG signals via the sensing electrode pairs 112. The sensing electrode pairs 112 may be, for example, dry electrodes. Regardless of the electrodes used to acquire the ECG signals, in some examples, the medical device 1600 includes ECG sensing electrode circuitry (e.g., as provided by the sensor interface 212 and the at least one processor 218) that is configured to process first and second ECG data generated from the first and second ECG signals using distinct ECG analysis processes (i.e., an abnormality detection process and an arrhythmia verification process). In these examples, the combination of the abnormality detection process and the arrhythmia verification process has an improved reliability over the abnormality detection process alone.

In some examples, the medical device controller 120 of the medical device 1600 includes a cardiac monitor (e.g., the cardiac monitor 214) and a treatment controller (e.g., the treatment controller 216). In these examples, the cardiac monitor and treatment controller are configured to execute monitoring and treatment processes that include the abnormality detection and arrhythmia verification processes. At least one example monitoring and treatment process 1700 that the cardiac monitor and the treatment controller are configured to execute is described further below with reference to FIG. 17.

Figure 17:
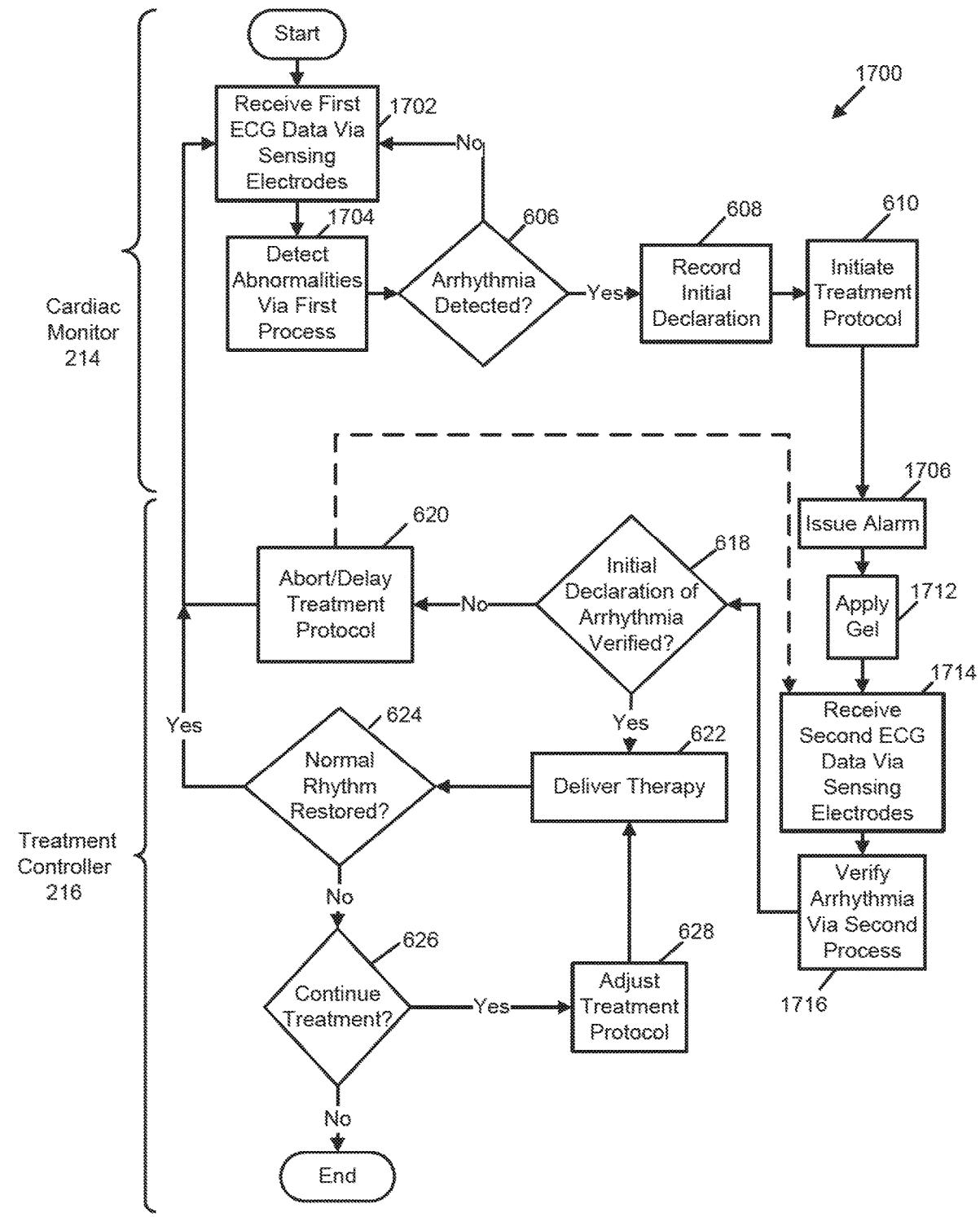
FIG. 17 depicts another monitoring and treatment process including arrhythmia verification in accordance with at least one example disclosed herein.

As shown in FIG. 17, the monitoring and treatment process 1700 includes the actions of the monitoring and treatment process 600. However, many of the details of the monitoring and treatment process 600 are omitted from the following description of the monitoring and treatment process 1700 for the sake of brevity. As illustrated in FIG. 17, the monitoring and treatment process 1700 starts with the cardiac monitor receiving 1702 first ECG data based on first ECG signals acquired by at least one first pair of sensing electrodes. In this example, the at least one first pair of sensing electrodes includes the sensing electrode pairs 112. In some examples, the act of receiving 1702 the first ECG data includes one or more of the acts described above with reference to the act 602.

Next, the cardiac monitor attempts to detect abnormalities 1704 in the first ECG data by executing an abnormality detection process as described above. In some examples, the act of detecting 1704 an abnormality includes one or more of the acts described above with reference to the act 604. Where the cardiac monitor does not detect 606 an arrhythmia condition of the patient, the cardiac monitor returns to receiving 1702 first ECG data. However, upon detecting 606 that the patient is experiencing an arrhythmia condition, the cardiac monitor records 608 an initial arrhythmia declaration and initiates 610*a* treatment protocol. In some examples, the treatment protocol includes issuance 1706 of an alarm of an impending therapeutic stimulation pulse.

In one example, after initiation 610 of the treatment protocol, the treatment controller controls, via a gel dispenser and associated circuitry, optional application 1712 of conductive gel between the patient's skin and a second pair of electrodes (e.g., the therapy electrode pair 114). The conductive gel may be applied between the second pair of electrodes and the skin of the patient prior to acquiring second ECG signals, as described herein. In some examples, the act of applying 1712 the conductive gel includes one or more of the acts described above with reference to the act 612.

The monitoring and treatment process 1700 continues with the treatment controller receiving 1714 second ECG data based on second ECG signals acquired by the pair of sensing electrodes 112. In some examples, the act of receiving 1714 the second ECG data includes one or more of the acts described above with reference to the act 614.

In some examples, the second ECG signals are acquired over a predefined period of time with a duration of between 5 and 10 seconds. In some examples, the duration varies with the type of arrhythmia condition detected. For instance, where the arrhythmia condition detected is ventricular tachycardia, the duration may span 8 to 10 seconds. However, where the arrhythmia condition detected is ventricular fibrillation, the duration may span 5 to 8 seconds.

Next, the treatment controller attempts to verify 1716 the declared arrhythmia using the second ECG data by executing an arrhythmia verification process. In an example, the verification 1716 of the second ECG data is accomplished by activating the ECG sensing electrode circuitry to execute the arrhythmia verification process and execution of the arrhythmia verification process results in a more reliable determination of whether or not the patient is experiencing an arrhythmia condition. In some examples, the act of verifying 1716 an arrhythmia includes one or more of the acts described above with reference to the act 616.

Where the treatment controller fails to verify 618 the declared arrhythmia condition, the treatment controller aborts or delays 620 the treatment protocol. This delay may have a duration of at least 30 seconds and, as shown in FIG. 17, the treatment controller may return to receiving and processing second ECG data during the delay. In some examples, in executing the arrhythmia verification process, the treatment controller may determine a value that indicates a confidence that the second ECG data reflects normal cardiac function of the patient. In some examples, the treatment controller evaluates this value (e.g., by comparing it to a threshold value) to contribute to the verification of the arrhythmia condition.

As described above, in some examples, the abnormality detection process includes a first set of sub-processes and the arrhythmia verification process includes a second set of sub-processes. The first set may include a number of sub-processes different from the second set. For instance, the first set may include more sub-processes than the second set. In some examples, the second set of sub-processes includes a heart rate detection sub-process and/or a signal morphology detection sub-process. In some examples, the first set of sub-processes includes an FFT and the second set of sub-processes omits the FFT. In other examples the first set of sub-processes and the second set of sub-processes may include other sub-processes and the examples disclosed herein are not limited to a particular mapping of sub-processes to the first and second sets of sub-processes.

Upon verifying 618 the arrhythmia declaration, the treatment controller delivers 622, in an attempt to restore a normal rhythm to the patient's heart, one or more therapeutic stimulation pulses as selected in response to the type of arrhythmia condition detected. This verification 618 may occur during a period of time in which treatment has been delayed 620 or may occur prior to any delay 620 of treatment.

After delivery 622 of the therapy, the treatment controller analyzes the second ECG signals to determine 624 whether a "normal" heart rhythm (i.e., not an arrhythmia condition) has been restored. If a normal rhythm has been restored, the treatment controller returns control to the cardiac monitor. However, if a normal rhythm has not been restored, the treatment controller determines whether or not treatment should be continued 626. If treatment can be continued 626, the treatment protocol may optionally be adjusted 628 to, for example, change the type of therapeutic stimulation pulse provided to the patient. If the treatment cannot be continued 626, the monitoring and treatment process 1700 ends.

Figure 18:
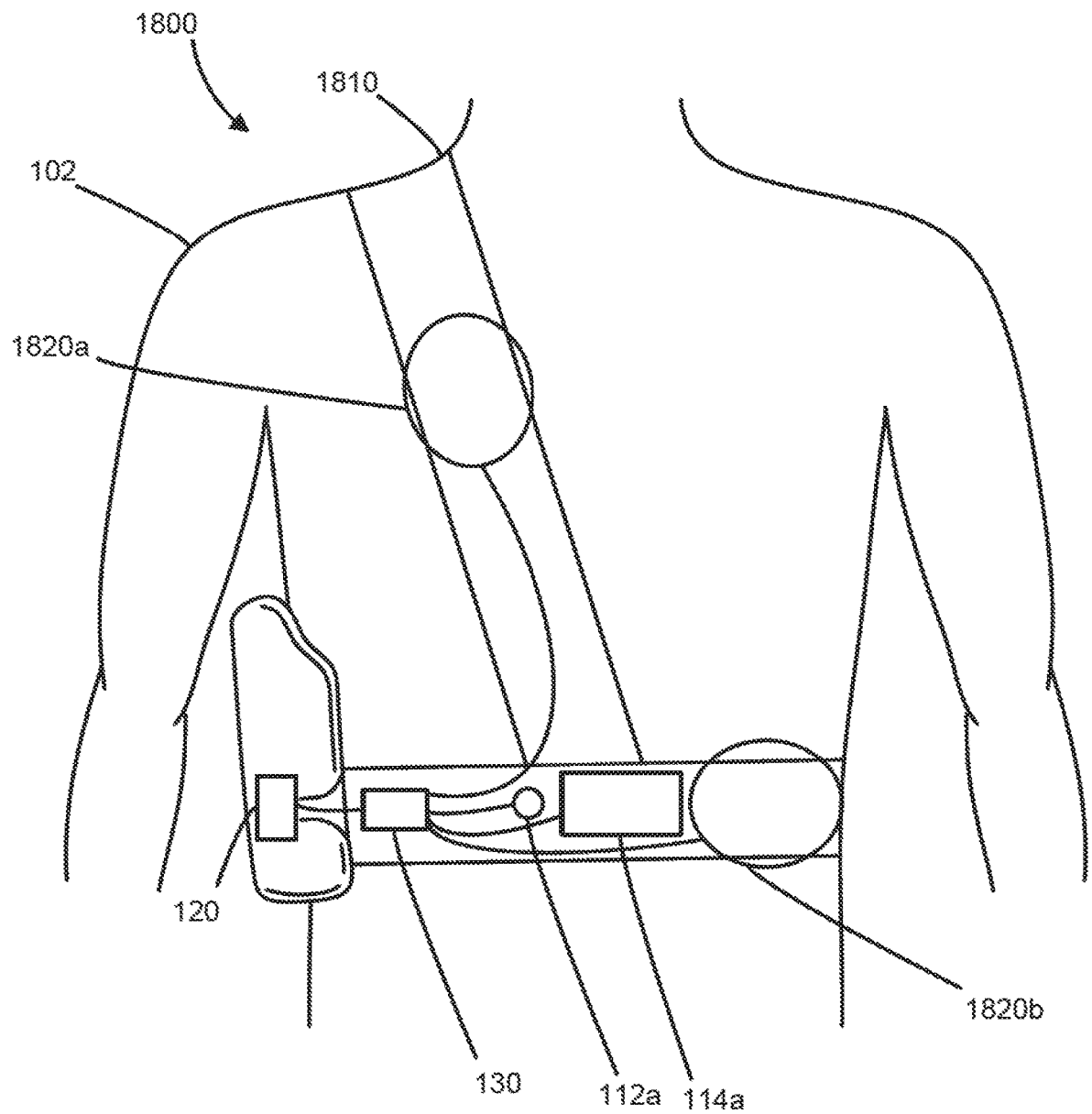
FIG. 18 depicts another wearable, ambulatory, external medical device in accordance with at least one example disclosed herein.

As shown, FIG. 18 includes a medical device 1800 that is external, ambulatory, and wearable by the patient 102. The medical device 1800 includes many of the components of the medical device 100 described above. For example, the medical device 1800 includes the therapy electrode pair 114 and the pairs of sensing electrodes 112, although only one of the anterior/posterior sensing electrodes 112a and the anterior therapy electrode 114a are shown. Each of the electrodes is configured to couple externally to a skin of the patient 102. The therapy electrode pair 114 is also configured to provide one or more therapeutic stimulation pulses to a heart of the patient 102 during execution of a treatment protocol. The sensing electrode pairs 112 are configured to couple externally to a skin of a patient and to acquire ECG signals of the patient 102. In certain implementations as described above, the medical device 1800 can be configured to acquire the ECG signals via the therapy electrodes 114 (e.g., configured as a multi-functional electrode) instead of or in addition to the sensing electrodes 112. The medical device 1800 also includes the medical device controller 120 and the connection pod 130. In addition, the medical device 1800 includes a garment 1810 and tensioners 1820a and 1820b.

In some examples, the tensioners 1820a and 1820b include electrical and/or mechanical components configured to tighten and/or loosen the garment 1810 around the patient. By tightening the garment 1810 around the patient, the tensioners 1820a and 1820b increase the quality of the electrical coupling between the patient's skin and the pairs of sensing electrodes 112, thereby improving the reliability of signals acquired thereby while the garment 1810 is tightened.

In some examples, the tensioners 1820a and 1820b include electromechanical components under control of the medical device controller 120, and more specifically, the processor 218 via sensor interface 212. For instance, in some examples, the tensioners 1820a and 1820b each include interior components like those of the electrode assemblies illustrated in FIGS. 3d-3g of U.S. Pat. No. 4,928,690 titled "PORTABLE DEVICE FOR SENSING CARDIAC FUNCTION AND AUTOMATICALLY DELIVERING ELECTRICAL THERAPY," which is hereby incorporated herein by reference in its entirety. In these examples, the processor 218 is configured to cause, as part of an arrhythmia verification process, the sensor interface 212 to electrically operate a release within the interior components to tighten the garment 1810 around the patient. This tightening improves reliability of signals acquired by the sensing electrodes 112.

Alternatively or additionally, in some examples, the garment 1810 includes tensile actuators composed of twist-spun nanofiber yarn and/or twist-inserted polymer fibers that generate tensile actuation when powered electrically, such as those described in International Patent Application Publication No. WO2014/022667, titled "COILED AND NON-COILED TWISTED NANOFIBER YARN AND POLYMER FIBER TORSIONAL AND TENSILE ACTUATORS," which is hereby incorporated herein by reference in its entirety. In these examples, the tensioners 1820a and 1820b each include electrical contacts coupled to the tensile actuators. Further, in these examples, the medical device controller 120, and more specifically, the processor 218 via the sensor interface 212, is configured to electrically power, as part of an arrhythmia verification process, the tensile actuators via the electrical contacts to tighten the garment 1810 around the patient. This tightening improves reliability of signals acquired by the sensing electrodes 112. Other examples of the tensioners 1820a and 1820b may be included within the medical device 1800 without departing from the scope of this disclosure.

In some examples, the medical device 1800 is configured to acquire first and second ECG signals via the sensing electrode pairs 112. The sensing electrode pairs 112 may be, for example, dry electrodes. Regardless of the electrodes used to acquire the ECG signals, in some examples, the medical device 1800 is configured to acquire the first ECG signals while the garment 1810 is not tightened and to acquire the second ECG signals while the garment 1810 is tightened. Further, in some examples, the medical device 1800 includes ECG sensing electrode circuitry (e.g., as provided by the sensor interface 212 and the at least one processor 218) that is configured to process first and second ECG data generated from the first and second ECG signals using distinct ECG analysis processes (i.e., an abnormality detection process and an arrhythmia verification process). In these examples, the combination of the abnormality detection process and the arrhythmia verification process has an improved reliability over the abnormality detection process alone, due at least in part to the higher quality electrical coupling created by tightening the garment 1810 around the patient.

In some examples, the medical device controller 120 of the medical device 1800 includes a cardiac monitor (e.g., the cardiac monitor 214) and a treatment controller (e.g., the treatment controller 216). In these examples, the cardiac monitor and treatment controller are configured to execute monitoring and treatment processes that include the abnormality detection and arrhythmia verification processes. At least one example monitoring and treatment process 1900 that the cardiac monitor and the treatment controller are configured to execute is described further below with reference to FIG. 19.

Figure 19:
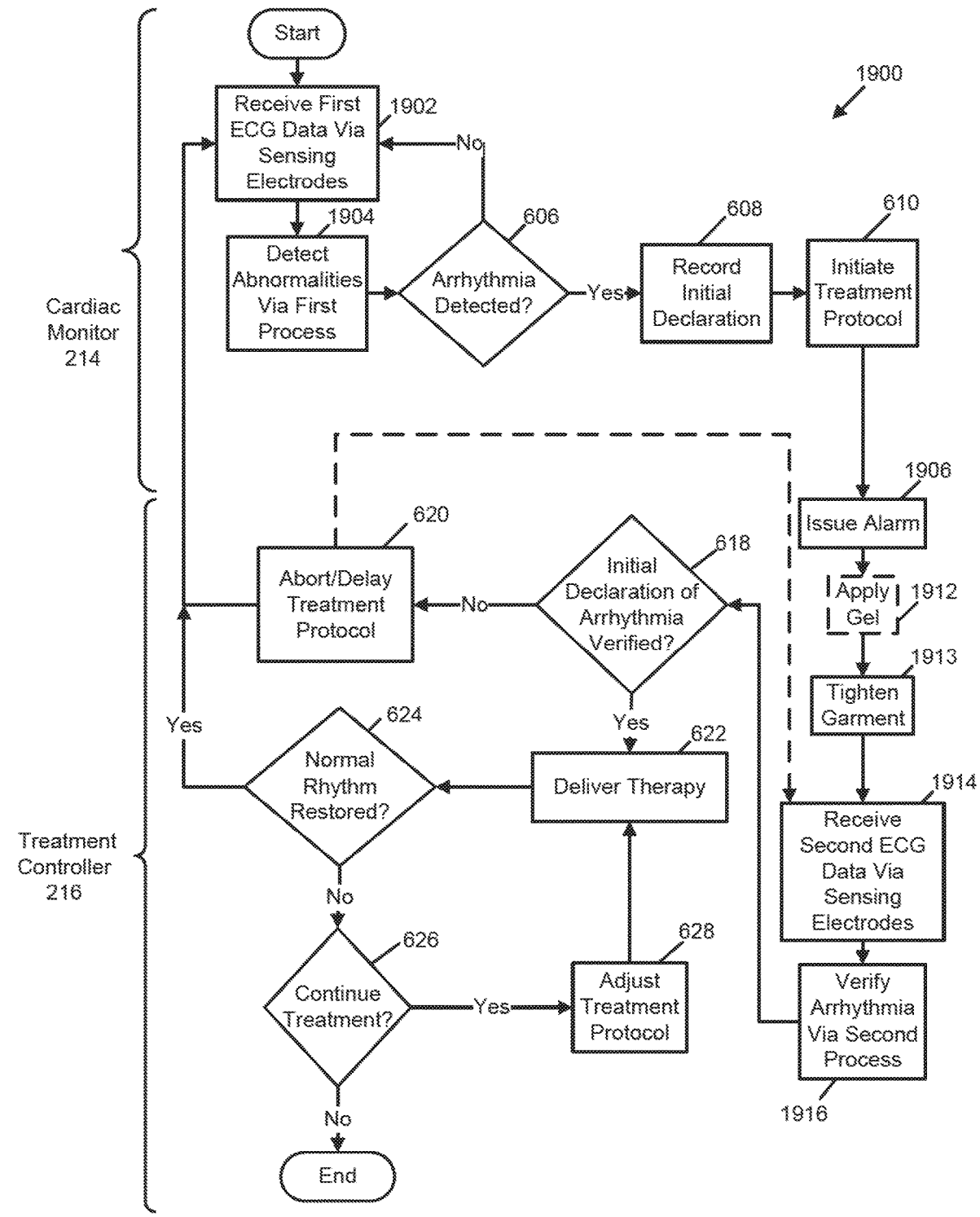
FIG. 19 depicts another monitoring and treatment process including arrhythmia verification in accordance with at least one example disclosed herein.

As shown in FIG. 19, the monitoring and treatment process 1900 includes the actions of the monitoring and treatment process 600. However, many of the details of the monitoring and treatment process 600 are omitted from the following description of the monitoring and treatment process 1900 for the sake of brevity. As illustrated in FIG. 19, the monitoring and treatment process 1900 starts with the cardiac monitor receiving 1902 first ECG data based on first ECG signals acquired by at least one first pair of sensing electrodes. In this example, the at least one first pair of sensing electrodes includes the sensing electrode pairs 112. In some examples, the act of receiving 1902 the first ECG data includes one or more of the acts described above with reference to the act 602.

Next, the cardiac monitor attempts to detect abnormalities 1904 in the first ECG data by executing an abnormality detection process as described above. In some examples, the act of detecting 1904 an abnormality includes one or more of the acts described above with reference to the act 604. Where the cardiac monitor does not detect 606 an arrhythmia condition of the patient, the cardiac monitor returns to receiving 1902 first ECG data. However, upon detecting 606 that the patient is experiencing an arrhythmia condition, the cardiac monitor records 608 an initial arrhythmia declaration and initiates 610a treatment protocol. In some examples, the treatment protocol includes issuance 1906 of an alarm of an impending therapeutic stimulation pulse.

In one example, after initiation 610 of the treatment protocol, the treatment controller controls, via a gel dispenser and associated circuitry, optional application 1912 of conductive gel between the patient's skin and the first pair of electrodes. The conductive gel may be applied between the first pair of electrodes and the skin of the patient prior to acquiring second ECG signals, as described herein. In some examples, the act of applying 1912 the conductive gel includes one or more of the acts described above with reference to the act 612. In some examples, the act 1912 of applying the conductive gel may be carried out after the verification of the arrhythmia in act 618.

In act 1913, the treatment controller controls one or more tensioners (e.g., the tensioners 1820a and 1820b), via associated circuitry (e.g., the sensor interface 212), to tighten a garment (e.g., the garment 1810) around the patient. For instance, the treatment controller may transmit (via the sensor interface) a control signal to the one or more tensioners to operate a release to apply tension to the garment and/or transmit a control signal to the one or more tensioners to power tensile actuators within the garment.

The monitoring and treatment process 1900 continues with the treatment controller receiving 1914 second ECG data based on second ECG signals acquired by the pair of sensing electrodes 112. In some examples, the act of receiving 1914 the second ECG data includes one or more of the acts described above with reference to the act 614.

In some examples, the second ECG signals are acquired over a predefined period of time with a duration of between 5 and 10 seconds. In some examples, the duration varies with the type of arrhythmia condition detected. For instance, where the arrhythmia condition detected is ventricular tachycardia, the duration may span 8 to 10 seconds. However, where the arrhythmia condition detected is ventricular fibrillation, the duration may span 5 to 8 seconds.

Next, the treatment controller attempts to verify 1916 the declared arrhythmia using the second ECG data by executing an arrhythmia verification process. In examples, the acts 1913, 1914 and 1916 can be together considered part of the arrhythmia verification process. The verification 1916 of the initial declaration of the arrhythmia based on the second ECG data can be accomplished by activating the ECG sensing electrode circuitry to execute the arrhythmia verification process. Execution of the arrhythmia verification process results in a more reliable determination of whether or not the patient is experiencing an arrhythmia condition. In some examples, the act of verifying 1916 an arrhythmia includes one or more of the acts described above with reference to the act 616 (see FIG. 6A and the example processes and sub-processes described in Table 1).

Where the treatment controller refutes or otherwise fails to verify 618 the declared arrhythmia condition, the treatment controller aborts or delays 620 the treatment protocol. This delay may have a duration of at least 30 to 45 seconds and, as shown in FIG. 19, the treatment controller may return to receiving and processing second ECG data during the delay. If via execution of the act 618 or during the delay period, the treatment controller determines that normal sinus rhythm has returned in the patient, the treatment protocol can be aborted and the medical device can return to a monitoring state via the cardiac monitor. In some examples, in executing the arrhythmia verification process, the treatment controller may determine a value that indicates a confidence that the second ECG data reflects normal cardiac function of the patient. In some examples, the treatment controller evaluates this value (e.g., by comparing it to a threshold value) to contribute to the verification of the arrhythmia condition.

As described above, in some examples, the abnormality detection process includes a first set of sub-processes and the arrhythmia verification process includes a second set of sub-processes. The first set may include a number of sub-processes different from the second set. For instance, the first set may include more sub-processes than the second set. In some examples, the second set of sub-processes includes a heart rate detection sub-process and/or a signal morphology detection sub-process. In some examples, the first set of sub-processes includes an FFT and the second set of sub-processes omits the FFT. In other examples the first set of sub-processes and the second set of sub-processes may include other sub-processes and the examples disclosed herein are not limited to a particular mapping of sub-processes to the first and second sets of sub-processes. Alternatively or additionally, in some examples, the first set of sub-processes and the second set of sub-processes may be identical, but, in these examples, the arrhythmia verification process may still provide improved reliability by virtue of the signals acquired while the garment is tightened around the patient.

Upon verifying 618 the arrhythmia declaration, the treatment controller delivers 622, in an attempt to restore a normal rhythm to the patient's heart, one or more therapeutic stimulation pulses as selected in response to the type of arrhythmia condition detected. This verification 618 may occur during a period of time in which treatment has been delayed 620 or may occur prior to any delay 620 of treatment.

After delivery 622 of the therapy, the treatment controller analyzes the second ECG signals to determine 624 whether a "normal" heart rhythm (e.g., a normal sinus rhythm) has been restored. If a normal rhythm has been restored, the treatment controller returns control to the cardiac monitor. However, if a normal rhythm has not been restored, the treatment controller determines whether or not treatment should be continued 626. If treatment can be continued 626, the treatment protocol may optionally be adjusted 628 to, for example, change the type of therapeutic stimulation pulse provided to the patient. If the treatment cannot be continued 626, the monitoring and treatment process 1900 ends.

Further Considerations

Although the subject matter contained herein has been described in detail for the purpose of illustration, it is to be understood that such detail is solely for that purpose and that the present disclosure is not limited to the disclosed examples, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

The invention claimed is:

1. A wearable cardioverter defibrillator device comprising:
   a pair of therapy electrodes configured to couple externally to a skin of a patient and to provide one or more therapeutic stimulation pulses to a heart of the patient during execution of a treatment protocol;
   a first pair of sensing electrodes configured to couple externally to the skin of the patient and to acquire first electrocardiogram (ECG) signals, wherein the first pair of sensing electrodes comprises dry sensing electrodes;
   a second pair of sensing electrodes distinct from the first pair of sensing electrodes and configured to couple externally to the skin of the patient, wherein the second pair of sensing electrodes is configured to be electrically coupled to the skin of the patient, and is configured to acquire, through a layer of conductive gel, second ECG signals having an improved reliability over the first ECG signals; and
   at least one processor coupled to the first pair of sensing electrodes, the second pair of sensing electrodes, and the pair of therapy electrodes and configured to
   receive first ECG data generated from the first ECG signals;
   analyze the first ECG data to detect an arrhythmia condition of the patient, wherein the arrhythmia condition comprises a ventricular tachycardia condition or a ventricular fibrillation condition;
   record an initial declaration of the ventricular tachycardia condition or the ventricular fibrillation condition of the patient in response to detecting the ventricular tachycardia condition or the ventricular fibrillation condition;
   initiate the treatment protocol in response to the initial declaration of the ventricular tachycardia condition or the ventricular fibrillation condition;
   receive second ECG data generated from the second ECG signals;
   analyze the second ECG data to verify the initial declaration of the ventricular tachycardia condition or the ventricular fibrillation condition; and
   control delivery of the one or more therapeutic stimulation pulses to the heart of the patient in response to verifying the initial declaration of the ventricular tachycardia condition or the ventricular fibrillation condition.

2. The wearable cardioverter defibrillator device of claim 1, wherein the at least one processor is further configured to abort the treatment protocol in response to detecting normal cardiac function based on analysis of the second ECG data.

3. The wearable cardioverter defibrillator device of claim 1, wherein the second pair of sensing electrodes comprises an electrically conductive sensing element configured to be electrically coupled to the skin of the patient via the layer of conductive gel.

4. The wearable cardioverter defibrillator device of claim 1, further comprising a gel dispenser, and wherein the gel dispenser is configured to dispose the layer of conductive gel between an electrically conductive element of the second pair of sensing electrodes and the skin of the patient.

5. The wearable cardioverter defibrillator device of claim 1, further comprising gel deployment circuitry coupled to the at least one processor, wherein the at least one processor is further configured to signal the gel deployment circuitry to cause at least one gel dispenser to apply the layer of conductive gel between the skin of the patient and the second pair of sensing electrodes in response to detecting the ventricular tachycardia condition or the ventricular fibrillation condition and prior to acquiring the second ECG signals.

6. The wearable cardioverter defibrillator device of claim 5, further comprising an electrode assembly that includes:
   at least one of the sensing electrodes included in the second pair of sensing electrodes and
   at least one of the gel dispensers included in the at least one gel dispenser.

7. The wearable cardioverter defibrillator device of claim 5, further comprising a therapy pad, the therapy pad comprising:
   the at least one gel dispenser,
   at least one of the therapy electrodes of the pair of therapy electrodes, and
   at least one of the sensing electrodes of the second pair of sensing electrodes.

8. The wearable cardioverter defibrillator device of claim 1, wherein the at least one processor is configured to analyze the first ECG data with an abnormality detection process and to analyze the second ECG data with an arrhythmia verification process.

9. The wearable cardioverter defibrillator device of claim 8, further comprising at least one non-ECG sensor, the at least one non-ECG sensor comprising one or more of an accelerometer and a photoplethysmograph sensor, wherein the at least one processor is further coupled to the at least one non-ECG sensor and is further configured to:
   receive non-ECG data generated from signals acquired by the at least one non-ECG sensor; and
   analyze the non-ECG data with the abnormality detection process to contribute to detection of the ventricular tachycardia condition or the ventricular fibrillation condition.

10. The wearable cardioverter defibrillator device of claim 1, wherein each of the second pair of sensing electrodes comprises an electrically conductive element configured to be electrically coupled to the skin of the patient via the conductive gel.

11. A wearable cardioverter defibrillator device comprising:
   a pair of therapy electrodes configured to couple externally to a skin of a patient and to provide one or more therapeutic stimulation pulses to a heart of the patient during execution of a treatment protocol;

a first pair of sensing electrodes configured to couple externally to the skin of the patient and to acquire first electrocardiogram (ECG) signals, wherein the first pair of sensing electrodes comprises dry sensing electrodes;

a second pair of sensing electrodes distinct from the first pair of sensing electrodes and configured to couple externally to the skin of the patient and to acquire second ECG signals;

gel deployment circuitry; and at least one processor coupled to the first pair of sensing electrodes, the second pair of sensing electrodes, the pair of therapy electrodes, and the gel deployment circuitry and configured to receive first ECG data generated from the first ECG signals, analyze the first ECG data to detect an arrhythmia condition of the patient, wherein the arrhythmia condition comprises a ventricular tachycardia condition or a ventricular fibrillation condition, record an initial declaration of the ventricular tachycardia condition or the ventricular fibrillation condition of the patient in response to detecting the ventricular tachycardia condition or the ventricular fibrillation condition, initiate the treatment protocol in response to the initial declaration of the ventricular tachycardia condition or the ventricular fibrillation condition, signal the gel deployment circuitry to cause at least one gel dispenser to apply conductive gel between the second pair of sensing electrodes and the skin of the patient prior to acquiring the second ECG signals, receive second ECG data generated from the second ECG signals after the conductive gel is applied between the second pair of sensing electrodes and the skin of the patient, analyze the second ECG data to verify the initial declaration of the ventricular tachycardia condition or the ventricular fibrillation condition, one or more of abort and delay the treatment protocol in response to at least one of detecting normal cardiac function and refuting the initial declaration of the ventricular tachycardia condition or the ventricular fibrillation condition based on analysis of the second ECG data, and control delivery of the one or more therapeutic stimulation pulses to the heart of the patient in response to verifying the initial declaration of the ventricular tachycardia condition or the ventricular fibrillation condition.

12. The wearable cardioverter defibrillator device of claim 11, wherein the second pair of sensing electrodes comprises conductive sensing electrodes.

13. The wearable cardioverter defibrillator device of claim 11, wherein each of the second pair of sensing electrodes comprises an electrically conductive element configured to be electrically coupled to the skin of the patient via the conductive gel.

\* \* \* \* \*